United States Patent
Housley et al.

(10) Patent No.: US 11,850,044 B2
(45) Date of Patent: Dec. 26, 2023

(54) NOISE-INDUCED HEARING LOSS SUSCEPTIBILITY TEST METHOD AND TEST APPARATUS

(71) Applicant: NewSouth Innovations Pty Limited, Sydney (AU)

(72) Inventors: Gary David Housley, Connells Point (AU); Jennie M. E. Cederholm, Coogee (AU)

(*) Notice: Subject to any disclaimer, the term of this patent is extended or adjusted under 35 U.S.C. 154(b) by 428 days.

(21) Appl. No.: 16/978,519

(22) PCT Filed: Mar. 6, 2019

(86) PCT No.: PCT/AU2019/050192
§ 371 (c)(1),
(2) Date: Sep. 4, 2020

(87) PCT Pub. No.: WO2019/169440
PCT Pub. Date: Sep. 12, 2019

(65) Prior Publication Data
US 2021/0015405 A1    Jan. 21, 2021

(30) Foreign Application Priority Data
Mar. 6, 2018   (AU) .................. 2018900727

(51) Int. Cl.
*A61B 5/12*    (2006.01)
*G16H 50/30*   (2018.01)
(Continued)

(52) U.S. Cl.
CPC .............. *A61B 5/125* (2013.01); *A61B 5/24* (2021.01); *A61B 5/291* (2021.01); *A61B 5/38* (2021.01);
(Continued)

(58) Field of Classification Search
CPC ........... A61B 5/125; A61B 5/24; A61B 5/291; A61B 5/38; A61B 5/4884; A61B 5/6817;
(Continued)

(56) References Cited

U.S. PATENT DOCUMENTS 5,916,174 A    6/1999  Dolphin
6,974,421 B1   12/2005 Causevic et al.
(Continued)

OTHER PUBLICATIONS

Judi A. Lapsley Miller et al., "Low-level otoacoustic emissions may predict susceptibility to noise-induced hearing loss", The Journal of the Acoustical Society of America, 120, 280-296, 2006 (Year: 2006).*

(Continued)

*Primary Examiner* — Eric F Winakur
*Assistant Examiner* — Jonathan Drew Moroneso
(74) *Attorney, Agent, or Firm* — Farber LLC

(57) ABSTRACT

An audiometric test method is provided where a noise stress test is applied to a subject, during the application of the noise stress test measuring one or more indicators reflecting a subjects purinergic hearing adaptation to noise exposure. The measured indicators are analysed to quantify degree of change and rate of change of the subjects purinergic hearing adaptation to noise exposure. An audiometric test system and audiometer configured to perform the test is also provided.

20 Claims, 16 Drawing Sheets

(51) Int. Cl.
- *A61B 5/38* (2021.01)
- *A61B 5/291* (2021.01)
- *A61B 5/24* (2021.01)
- *A61B 5/00* (2006.01)
- *A61B 5/246* (2021.01)
- *A61B 5/055* (2006.01)

(52) U.S. Cl.
CPC .......... *A61B 5/4884* (2013.01); *A61B 5/6817* (2013.01); *A61B 5/7282* (2013.01); *G16H 50/30* (2018.01); *A61B 5/055* (2013.01); *A61B 5/246* (2021.01); *A61B 2503/20* (2013.01)

(58) Field of Classification Search
CPC ....... A61B 5/7282; A61B 5/055; A61B 5/246; A61B 2503/20; A61B 5/12; G16H 50/30
See application file for complete search history.

(56) References Cited

U.S. PATENT DOCUMENTS

| | | | |
|---|---|---|---|
| 7,223,245 | B2 | 5/2007 | Zoth et al. |
| 2003/0073920 | A1 | 4/2003 | Smits et al. |
| 2014/0114209 | A1 | 4/2014 | Lodwig |
| 2017/0150909 | A1 | 6/2017 | Dalhoff et al. |
| 2018/0064374 | A1* | 3/2018 | Givens .................. G16H 40/63 |
| 2018/0160984 | A1* | 6/2018 | Mauger ................. G16H 50/30 |
| 2019/0289409 | A1* | 9/2019 | Greenberg ........... H04R 25/554 |

OTHER PUBLICATIONS

Dalhoff et al., "Distortion product otoacoustic emissions measured as vibration on the eardrum of human subjects", PNAS, 104, p. 1546-1551, 2007 (Year: 2007).*

European Patent Office; Extended European Search Report; European Patent Application No. 19763893.5; dated Dec. 11, 2020.

Housley, et al.; "ATP-gated ion channels mediate adaptation to elevated sound levels", PNAS, vol. 110, No. 18, pp. 7494-7499, Apr. 30, 2013.

Housley et al.; 10.1073/pnas.1222295110, retrieved from [http://www.pnas.org/lookup/suppl/doi: 10.1073/pnas. 1222295110/-/DCSupplemental], published on Apr. 30, 2013 together with D 1.L online supporting information to 01 as noted in 01 p. 7494.

Purines 2018 Basic and Translational Science on Purinergic Signaling and its Components for a Healthy and Better World. Purinergic Signalling 14 (Suppl 1), 1-122 (2018); See pp. S62 and S63. https://doi.org/10.1007/s11302-018-9637-0.

Cederholm, et al., Purinergic Signalling (2019) 14:S1-S122; pp. S62, S63.

* cited by examiner

NOISE-INDUCED HEARING LOSS SUSCEPTIBILITY TEST METHOD AND TEST APPARATUS

CROSS-REFERENCE TO RELATED APPLICATIONS

This application is a U.S. National Stage application of International Application No. PCT/AU2019/050192, filed Mar. 6, 2019, which claims priority to Australian Patent Application No. 2018900727, filed Mar. 6, 2018, the contents of which are hereby incorporated by reference in their entireties.

TECHNICAL FIELD

The field of the invention is auditory testing, in particular testing related to hearing loss.

BACKGROUND

Noise-induced hearing loss, also referred to as "industrial deafness" is a known problem. Our hearing normally accommodates a dynamic soundscape that ranges from very low to high intensities. However, acoustic overstimulation from a range of environmental (for example, recreational music) and occupational sources (for example, machine noise) can accelerate hearing loss. Treatment of hearing loss is problematic as the hair cells that transduce sound and the spiral ganglion neurons that transmit auditory information to the central nervous system (CNS) cannot be regenerated and there are currently no effective treatments outside use of auditory prostheses.

Many organizations where noise is routinely encountered above the nominal legislated ceiling of 85 dBA (A-weighted sound pressure level; averaged 8 hours daily exposure) undertake regular hearing tests on their employees. This includes the airline industry, heavy industry and the military, and routinely identifies individuals who have evidence of progressive hearing loss (elevation of pure tone audiometry thresholds). This hearing loss can be considered permanent and if this reaches 20 dB HL (hearing loss) it is considered clinically significant and the person is likely to be referred for assessment for an auditory prosthesis (hearing aid). In moderate to severe hearing loss, this may result in loss of employment and profound personal and social impact. In the US military, hearing loss is the principal reason for early discharge and represents an enormous cost to operations in addition to the profound social impact. Hearing loss is the third most chronic health problem in the USA and hearing loss and associated tinnitus is the most prevalent service connected disability in the US military.

Acoustic overstimulation, depending on frequency, level and duration, leads to a continuum of temporary or permanent sensorineural hearing loss. The mechanisms underlying development of reversible noise induced changes in our hearing sensitivity, which are intrinsically protective, involve a range of cochlear elements, including the ossicular chain middle ear reflex and inhibitory olivocochlear efferent feedback to the outer hair cells. A major additional mechanism is purinergic hearing adaptation mediated by acoustically-induced release of ATP in the cochlea that activates $P2X_2$ receptors ($P2X_2R$). These receptors, which assemble as trimeric ATP-gated non-selective cation channels, are broadly expressed in the cochlea, with prominent expression by cochlear partition epithelial cells, including the organ of the Corti, inner and outer sulcus and Reissner's membrane. Spiral ganglion neurons also express $P2X_2R$ alongside other P2X subtypes. $P2X_2R$ expression is upregulated in both the spiral ganglion and cochlear duct with noise exposure.

Studies have shown that susceptibility to noise-induced hearing loss can be influenced by genetic variability, based on absence of normal functioning $P2X_2$ receptors. Broadly, impairment of the purinergic signalling cascade that results in activation of the $P2X_2$ receptors may also increase susceptibility to noise-induced hearing loss. This includes mechanisms associated with noise-induced release of ATP from the cochlear tissue and ecto-ATPase-dependent breakdown of the ATP. These factors likely contribute to a continuum of individual vulnerability to NIHL. There is a need for detection of predisposition to noise-induced hearing loss to enable additional protective measures to be applied.

SUMMARY OF THE INVENTION

According to one broad aspect there is provided an audiometric test method comprising: applying a noise stress test to a subject; during the application of the noise stress test measuring one or more indicators reflecting a subject's purinergic hearing adaptation to noise exposure; and analysing the measured indicators to quantify degree of change and rate of change of the subject's purinergic hearing adaptation to noise exposure.

In an embodiment one of the measured indicators is otoacoustic emissions, and analysing the measured otoacoustic emissions to quantify change in amplitude and rate of change of the otoacoustic emissions during noise exposure.

In an embodiment the test further comprises the steps of quantifying the subject's reduction in noise sensitivity over the course of the noise stress test based on the subject's otoacoustic emissions and outputting a measure indicative of the subject's vulnerability to noise-induced hearing loss.

In an embodiment the noise stress test comprises one or more iterations of concurrently presenting two pure tones separated by a defined ratio (f1:f2) for a predetermined time period. Measuring can be performed using a microphone to collect sound from the outer ear canal to measure a third tone (f3) which is a resultant distortion product otoacoustic emission (DPOAE) stimulated by the presented tones (f1, f2).

In an embodiment the ratio of the two DPOAE probe tones is 1.2 (f1=1.2f2).

In an embodiment the readout of cochlear function during the noise stress test comprises two or more iterations with the intensity of the presented tones incremented between iterations. In an embodiment the noise stress test uses asymmetric intensities for the two pure tones. For example, there may be a relative intensity difference of 3-20 bB between the two tones. In a further embodiment, the DPOAE emission spectrum may be captured as a sweep across a broad frequency range.

In an embodiment the noise stress test comprises application of noise stimulus comprising any one of: white noise, Gaussian noise, pink noise, pure tones, clicks, or any combination thereof, or a combination of sampled sounds of natural or synthetic source, which may be of constant or modulated intensity.

In an embodiment the noise stress test further comprises an initial step of identifying a threshold intensity for the subject to elicit measurable DPOAE responses, and setting initial intensity levels for the noise stress test based on this threshold.

In one example the threshold intensity is determined by applying a sound signal having increasing intensity and using a microphone to record elicited DPOAE response.

In another embodiment the measurement of the change in cochlear function in response to a noise stressor may be a variation of otoacoustic emission (OAE) measurement other than DPOAE, such as stimulus frequency OAEs (SFOAEs) and transient-evoked OAEs (TEOAEs).

In another example the measurement of change in cochlear function during the noise stress test is determined by applying a sound signal having increasing intensity and using a camera or other non-auditory pickup such as laser Doppler or ultrasonics to monitor for an elicited response within the outer, middle or inner ear.

In another embodiment, the measure of change in cochlear function during the noise stress test is determined indirectly by measuring altered auditory-related brain function. Such auditory-related brain function may be determined using electrophysiological measurements, such as with auditory brainstem responses (ABR).

In another embodiment, hearing adaptation in response to a noise stress test may be recorded using spectral imaging of markers of brain activity, where such imaging may utilise excitation and emission across the expanse of the electromagnetic spectrum. Examples of this may include, and are not exclusive to, the use of infrared spectral imaging of regional brain oxygenation dynamics related to acoustic stimulation, functional magnetic resonance imaging (fMRI) or magnetoencephalography (MEG)—imaging of auditory brain function.

In an embodiment a noise adaptation index is applied to determine a measure indicative of the subject's vulnerability to noise-induced hearing loss based on the subject's reduction in noise sensitivity over the course of the noise stress test.

In an embodiment the test method further comprises measuring the auditory brainstem response (ABR) during the noise stress test. The ABR measurement of hearing function during the noise stress test may be used in conjunction with contemporaneous inclusion of otoacoustic emission measurements to provide an integrated measure of changing cochlear sound transduction and neurotransmission in response to the noise stress test.

According to another broad aspect there is provided an audiometric test method comprising: applying a noise stress test to a subject; during the application of the noise stress test measuring a subject's auditory brainstem response (ABR); analysing the measured ABR to quantify extent and rate of change during noise exposure. The sound used to evoke the ABR responses may be of a variety of modes and durations, for example transient sounds defined as clicks, or brief puretone sounds (at a specific or narrow-band frequency) known as tonepips.

For example, the ABR can be measured using either penetrating or surface electrodes.

According to another broad aspect there is provided an audiometer comprising: a probe configured for insertion into the external ear canal of a subject, the probe having a microphone to detect DPOAE response to noise stimulus and channels for delivering multiple sounds to the ear canal to stimulate the otoacoustic emissions; a sound generator configured to deliver noise stimulus to the subject; and a processor configured to drive the sound generator to deliver noise stimulus, and analyse received DPOAE response to quantify change in amplitude and rate of change of the DPOAE during noise exposure.

In an embodiment the audiometer processor is further configured to quantifying the subject's reduction in noise sensitivity over the course of the noise stress test and outputting a measure indicative of the subject's vulnerability to noise-induced hearing loss.

In an embodiment the audiometer processor is configured to wherein apply a noise adaptation index to determine a measure indicative of the subject's vulnerability to noise-induced hearing loss based on the subject's reduction in noise sensitivity over the course of the noise stress test.

In an embodiment the audiometer processor is in data communication with a data store storing data audiometric population weighting data and the processor is further configured to determine based on audiometric population weightings the significance of an individual's adaptive response to the noise stress with regard to vulnerability to noise-induced hearing loss, and a weighting for the personalized genetic or transcriptomic profile of the individual with regard to genetic variability screens impacting on hearing loss, including variability in elements of purinergic hearing adaptation.

Another broad aspect provides an audiometric test system comprising: a sound generator configured to deliver noise stimulus to a subject; one or more sensor modules configured to record data measuring one or more indicators reflecting a subject's purinergic hearing adaptation to noise exposure; and a processor configured to drive the sound generator to deliver noise stimulus, receive the recorded data and analyse the data to quantify for one or more of the measured indicators degree of change and rate of change, and output data quantifying the subject's purinergic hearing adaptation to noise exposure. In an embodiment at least one of the one or more sensor modules are provided on a probe configured for insertion into the external ear canal of the subject.

BRIEF DESCRIPTION OF THE DRAWINGS

An embodiment, incorporating all aspects of the invention, will now be described by way of example only with reference to the accompanying drawings in which.

Figure 7:
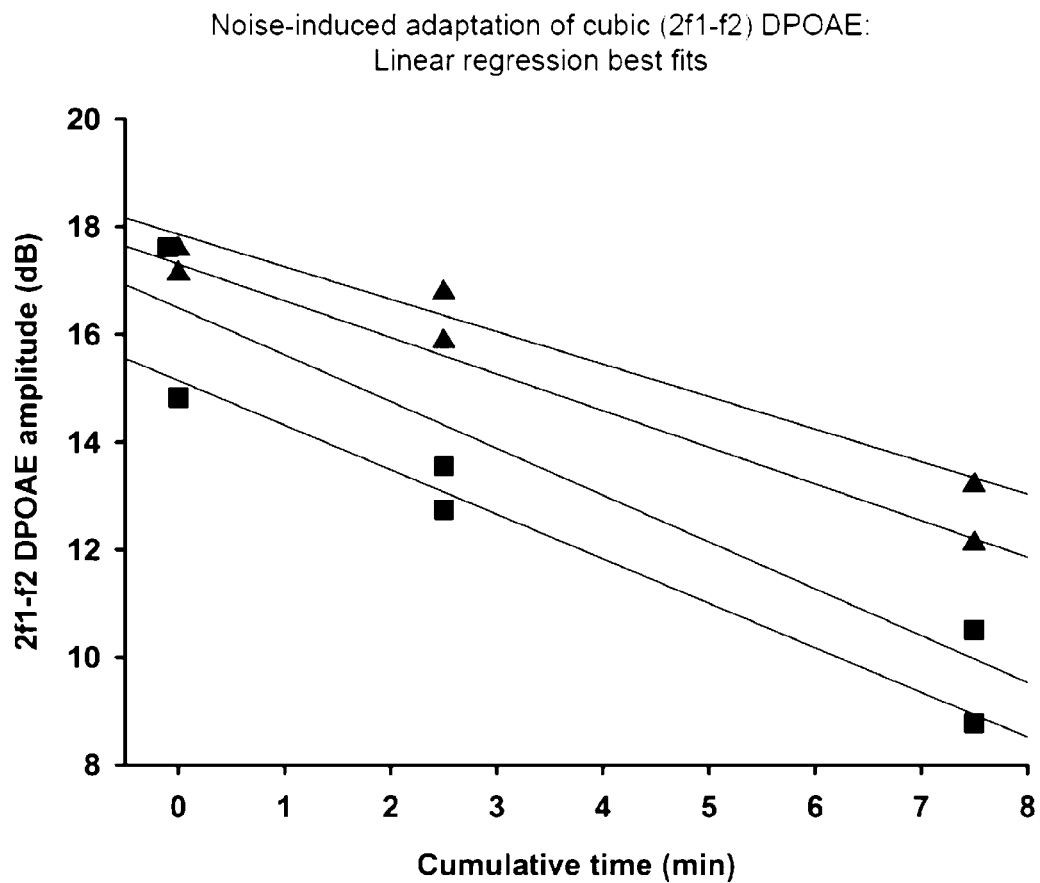
Figure 8:
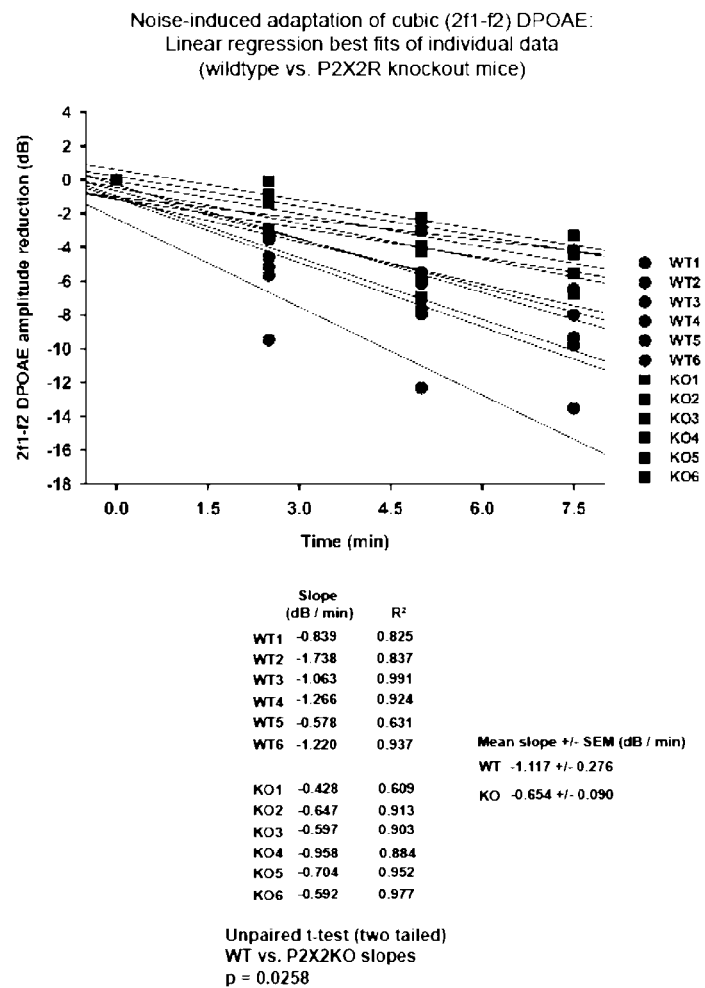

FIG. 7 is a graph showing the least squares linear regression best-fits for the adaptation rate of the cubic (2f1−f2; about 4 kHz) DPOAE signal during noise exposure in a human subject at two noise levels (92 dB SPL and 98 dB SPL; bandpass 2.5-4 kHz white noise);

FIG. 8 shows individual best fit linear regression plots of noise-induced adaptation of the cubic (2f1−f2; about 16 kHz; f1=f2, 60 dB SPL probe intensity) DPOAE in groups of wildtype and $P2X_2$ receptor knockout mice; band-pass noise (9-32 kHz white noise, 85 dB SPL).

Figure 9:
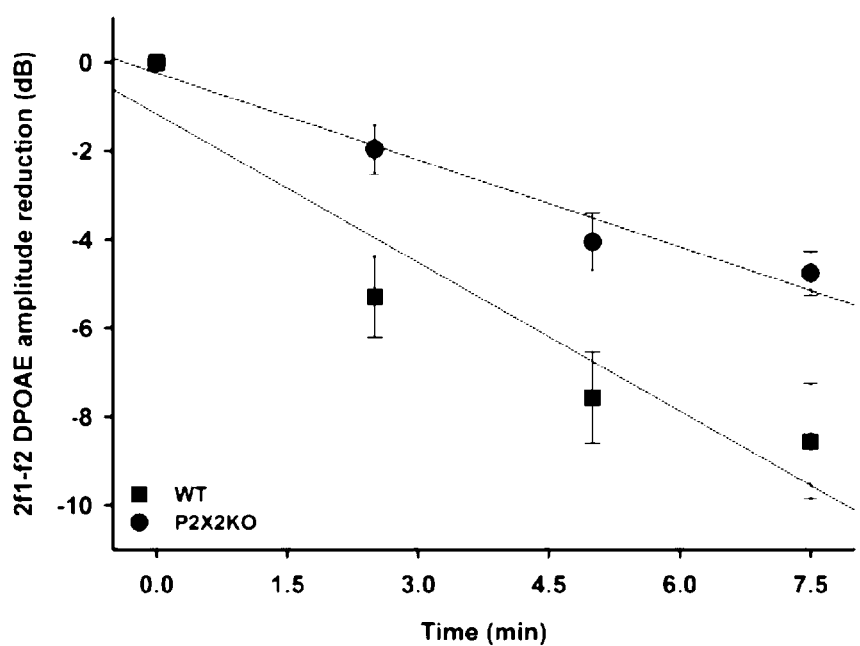

FIG. 9 shows average best fit linear regression plots of noise-induced adaptation of the cubic (2f1−f2) DPOAE in groups of wildtype and $P2X_2$ receptor knockout mice; (2f1−f2; about 16 kHz; f1=f2, 60 dB SPL probe intensity); band-pass noise (9-32 kHz white noise, 85 dB SPL); n=6 per genotype.

Figure 10A:
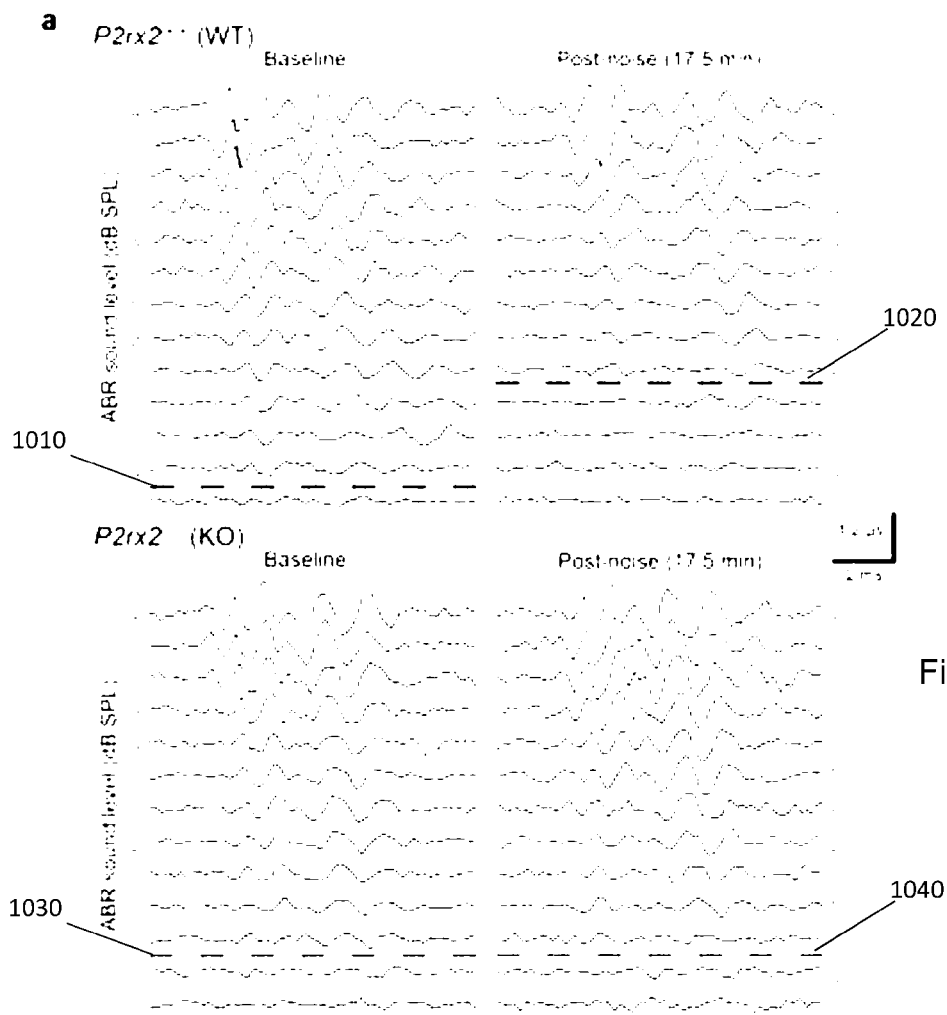
Figure 10B:
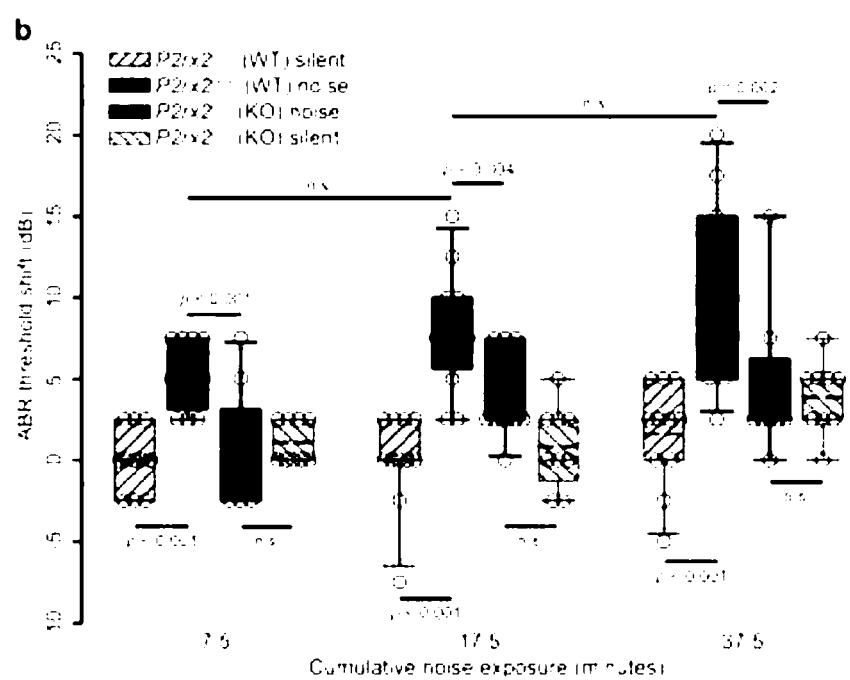
Figure 11:
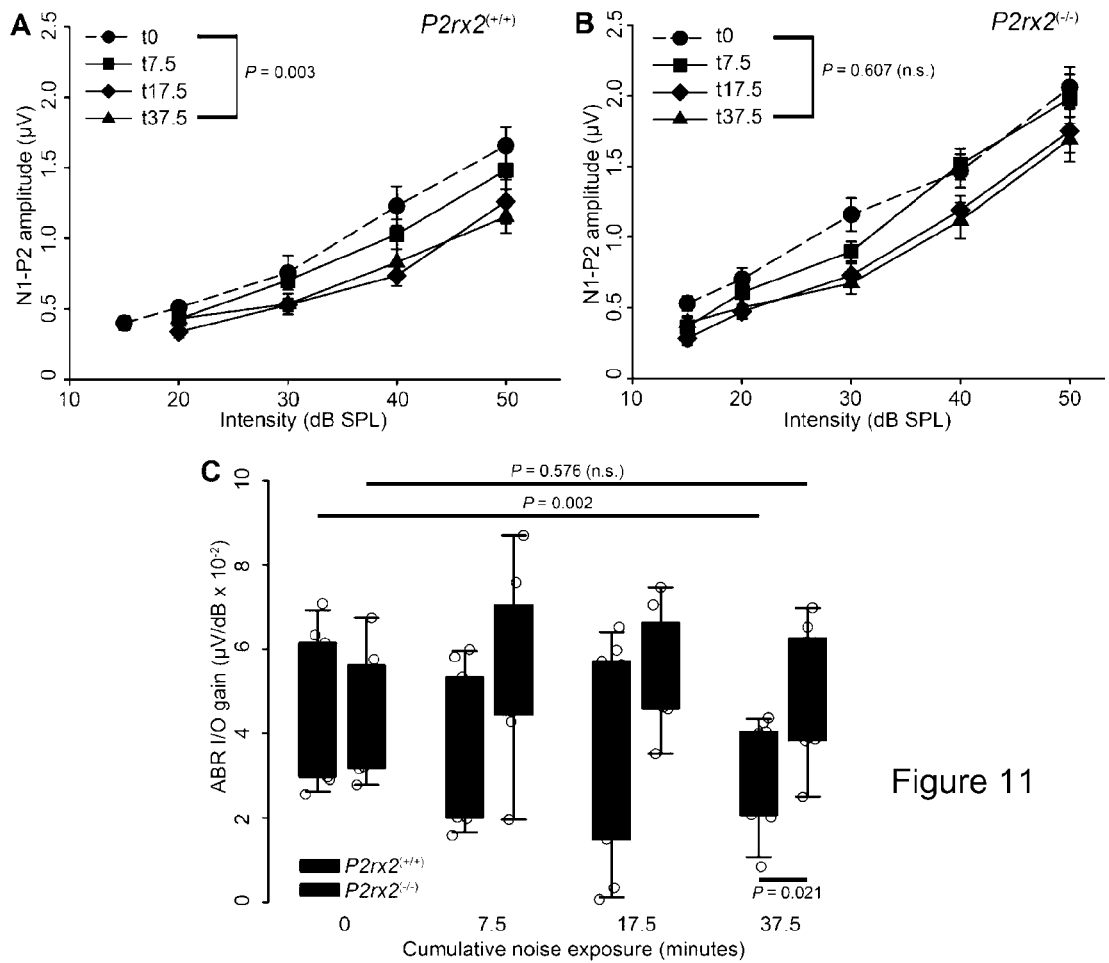
Figure 12:
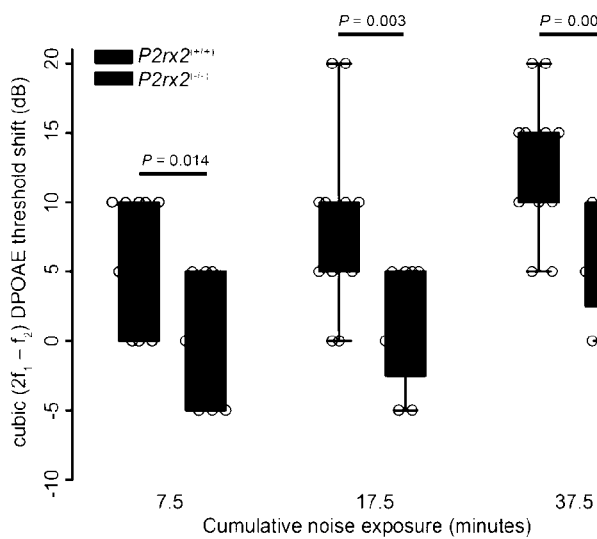
Figure 13:
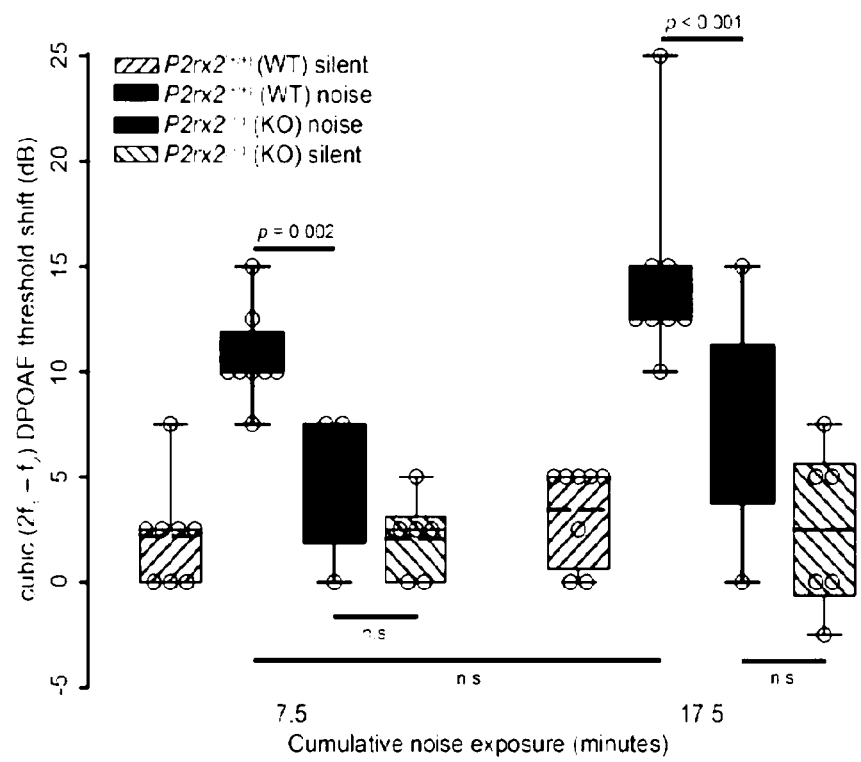
Figure 14:
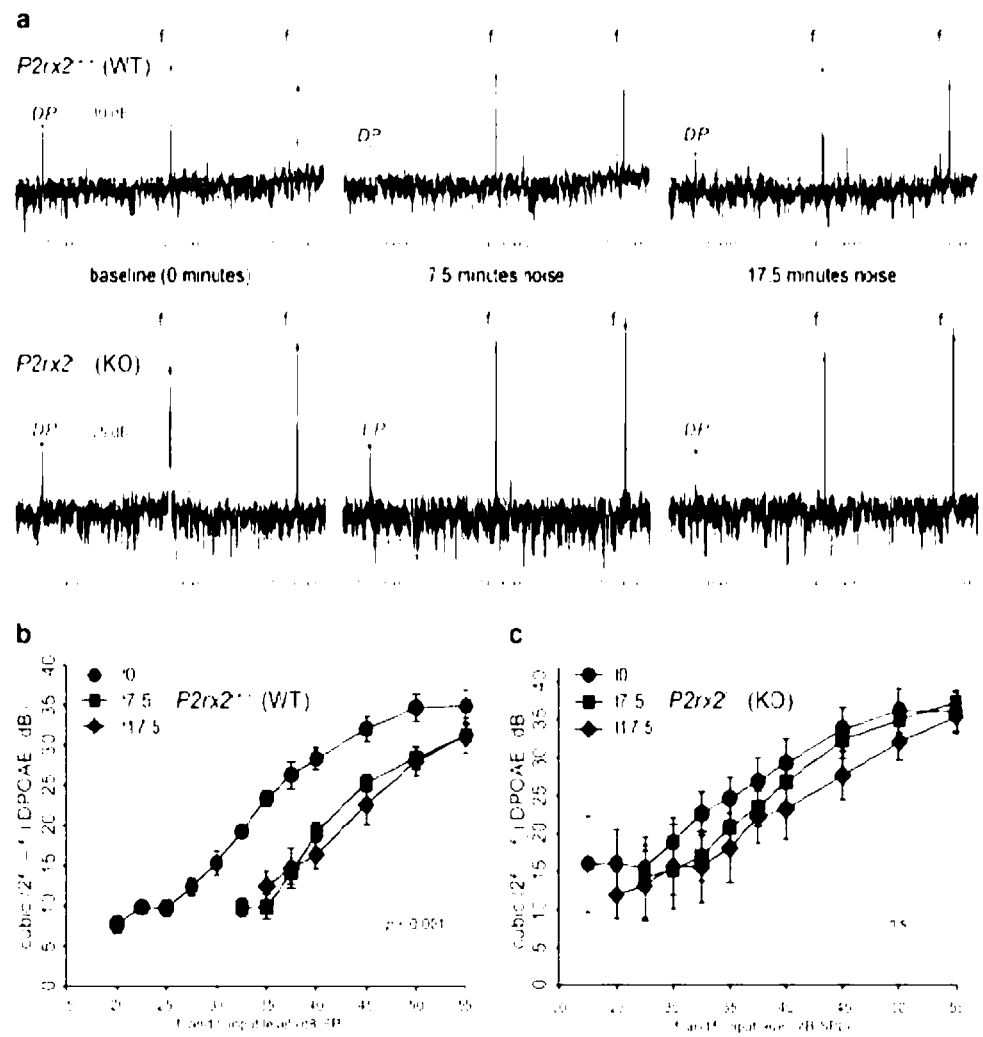
Figure 15:
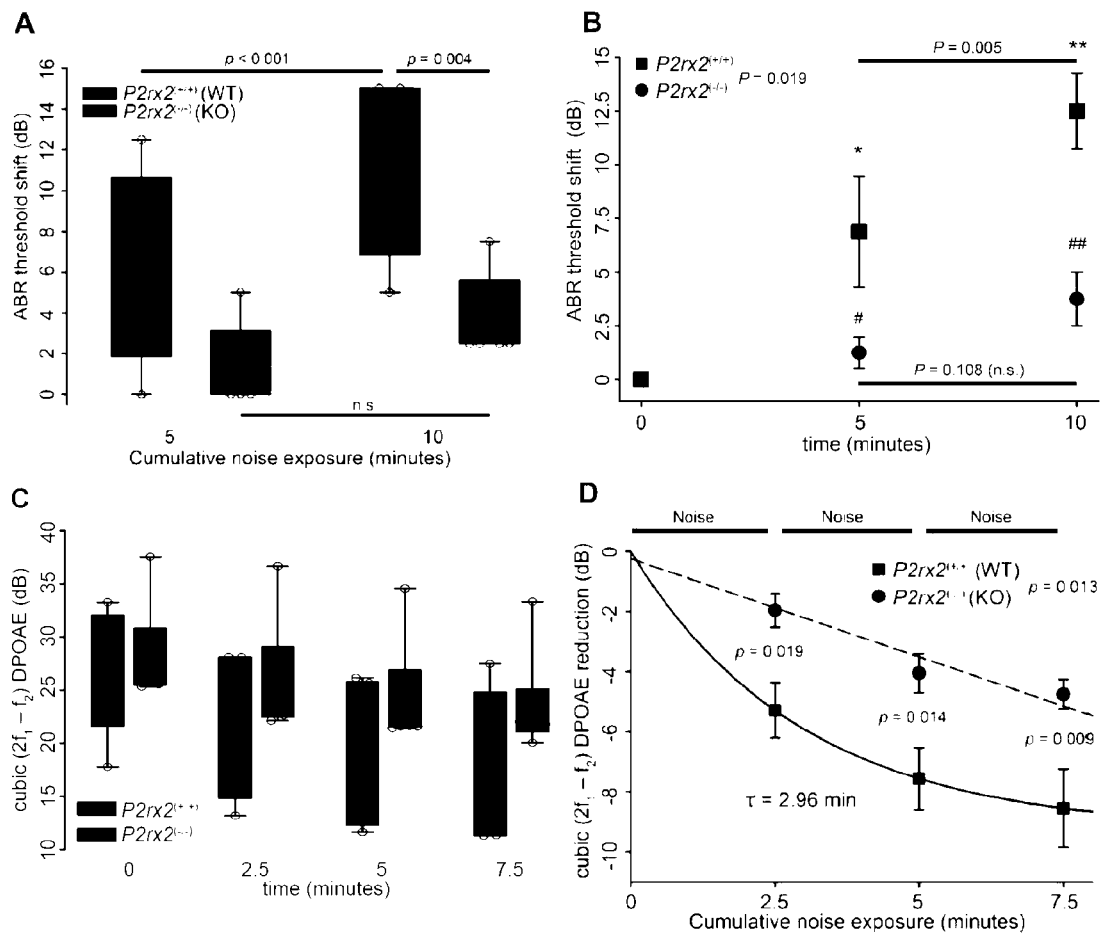

FIG. 10a shows graphs of ABR measurements for P2rx2 (+/+) mice and P2rx2(−/−) mice before and after exposure to moderate noise (85 dB SPL 8-32 kHz);

FIG. 10b shows boxplots for the ABR measurements of FIG. 10a with data overlay (open circles) of the ABR threshold shifts after 7.5 minutes, 17.5 minutes and 37.5 minutes cumulative noise exposures (filled boxes), or no-noise (silent) controls (diagonally striped boxes) assessed using a 16 kHz tone pip stimulus (P2rx2(+/+), n=11; P2rx2 (−/−), n=9);

FIG. 11 shows ABR input/output (I/O) growth functions and gain for P2rx2(+/+) and P2rx2(−/−) mice based on the amplitude of the N1-P2 wave (indicated in FIG. 10a);

FIG. 12 shows boxplots with data overlay (open circles) of the cubic (2f1−f2) DPOAE threshold shifts showing that P2rx2(+/+) mice (filled blue boxes) are significantly different to P2rx2(−/−) mice (filled red boxes) after 7.5, 17.5 and 37.5 minutes noise exposure (85 dB SPL 8-32 kHz);

FIG. 13 shows boxplots with data overlay (open circles) of the cubic (2f1−f2) DPOAE threshold shifts showing that P2rx2(+/+) mice (filled blue boxes) are significantly different to P2rx2(−/−) mice (filled red spotted boxes) after 7.5 and 17.5 minutes noise exposure (85 dB SPL 8-32 kHz); note that the P2rx2(−/−) mice threshold shifts were indistinguishable from the no-noise (silent) control group (red diagonals);

FIG. 14 shows P2rx2(−/−) mice (KO) lack the reduction in cubic DPOAE amplitude during noise exposure (85 dB SPL, 8-32 kHz) evident across a range of probe tone (f1 and f2) intensities (growth function. Adaptation (reduction in DPOAE amplitude) occurs in the first 7.5 minutes in the wildtype (WT) P2rx2(+/+) mice, and no adaptation occurs in the mice null for the P2rx2 gene encoding the P2X2 receptor (P2rx2(−/−), KO); and FIG. 15 shows the time course for development of noise-induced ABR threshold shifts (A and B) and cubic (2f1−f2) DPOAE amplitude reduction (C and D); The noise stressor was 85 dB SPL (9-32 kHz white noise); ABR responses were elicited by 16 kHz tonepips; DPOAE measurements used f1=f2 at 60 dB probe intensity, about 16 kHz.

Figure 16:
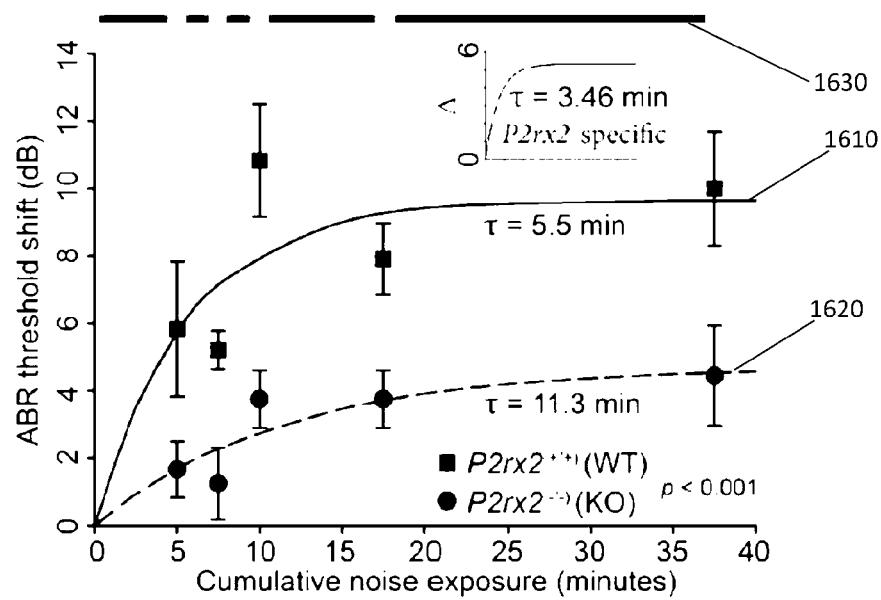

FIG. 16 is a graph modelling kinetics of purinergic adaptation from ABR threshold shifts during noise exposure; inset shows the WT (adapting) response subtracted from the baseline (P2rx2 KO) data.

Figure 17:
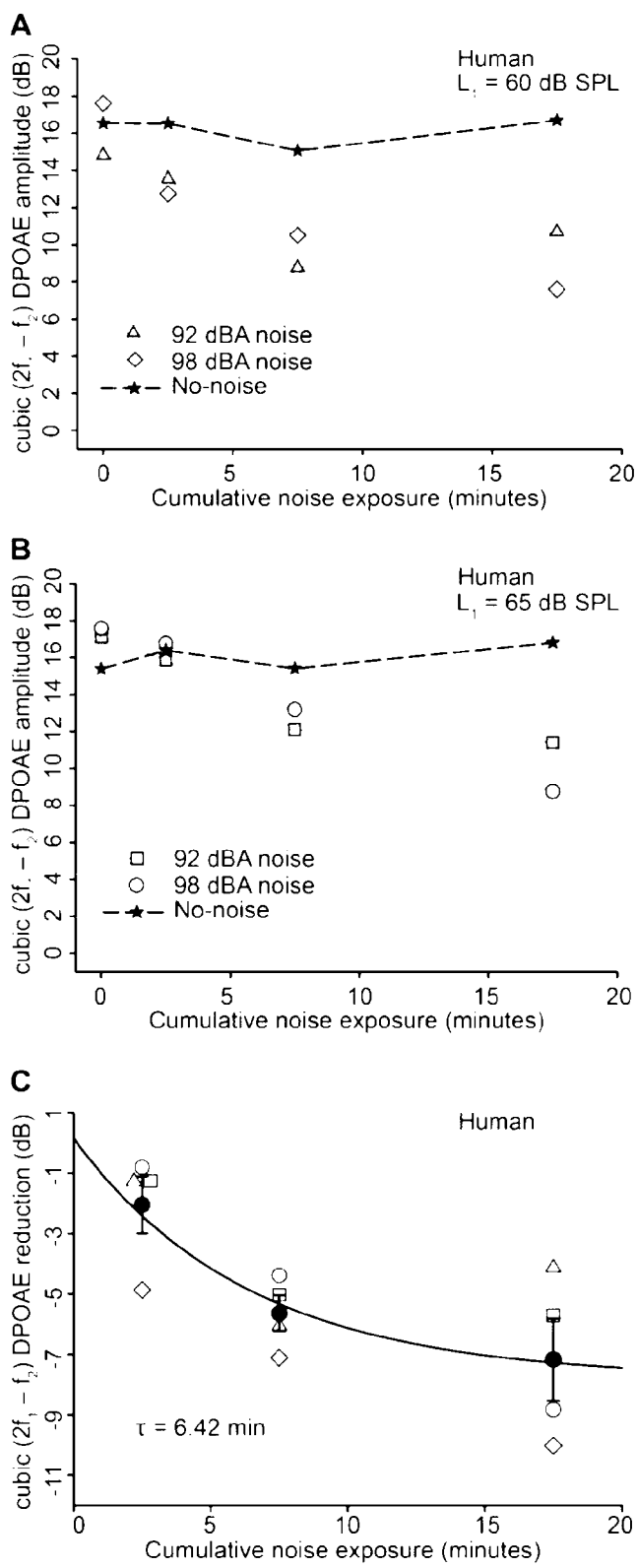
Figure 18:
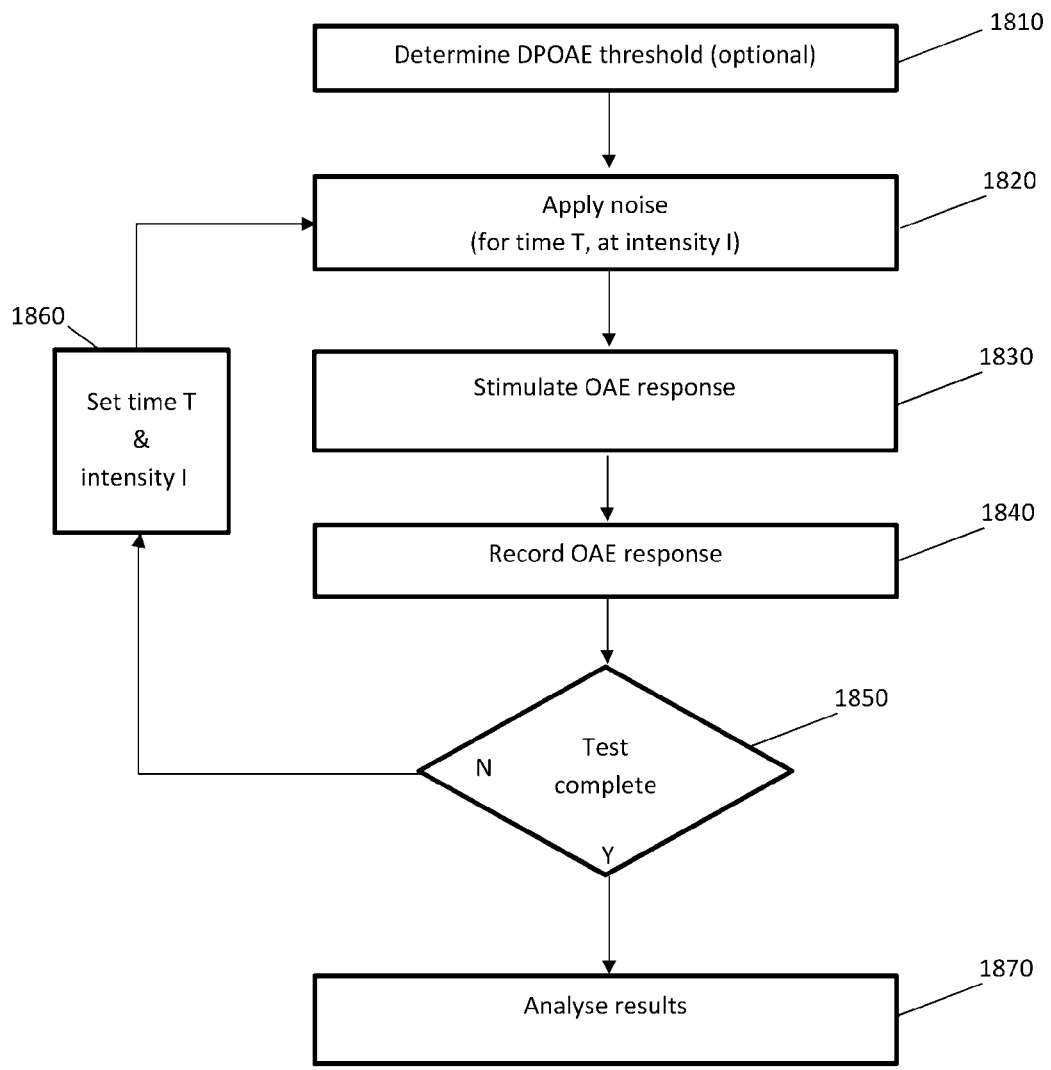

FIG. 17 shows development of the cubic (2f1−f2) DPOAE adaptation (about 4 kHz) with noise exposure in a human subject during two noise stress test intensities (2.5-4 kHz white noise); average of 3 trials per condition for data shown in A and B. C shows the single exponential decay function best fit to the combined data FIG. 18 is a flowchart of an example of a test process in accordance with an embodiment of the invention based on otoacoustic emission characterisation of cochlear function.

BRIEF DESCRIPTION OF THE TABLES

Table 1: Statistical comparison of 16 kHz ABR threshold shifts with noise exposure (85 dB SPL, 8-32 kHz white noise) in mice, for Study 1.

Table 2: Statistical comparison of 16 kHz ABR growth function (I/O gain) for 85 dB SPL white noise (8-32 kHz) in mice for Study 1.

Table 3: Statistical comparison of 16 kHz cubic (2f1−f2) DPOAE threshold shifts with ketamine/xylazine/acepromazine anaesthetic in mice; 85 dB SPL white noise (8-32 kHz), for Study 1.

Table 4: Statistical comparison of 16 k Hz cubic (2f1−f2) DPOAE threshold shifts with isoflurane anaesthetic in mice; 85 dB SPL white noise (8-32 kHz for Study 2.

Table 5: Statistical comparison of 16 k Hz cubic (2f1−f2) DPOAE amplitudes and growth function in mice with isoflurane anaesthetic; 85 dB SPL white noise (8-32 kHz, for Study 2.

Table 6: Statistical comparison of 16 kHz ABR thresholds and threshold shifts with 85 dB SPL white noise (9-32 kHz), for Study 3.

Table 7: Statistical comparison 16 kHz cubic (2f1−f2) DPOAE amplitudes and reduction with 85 dB SPL white noise (9-32 kHz) at 60 dB SPL probe intensity, for Study 3.

DETAILED DESCRIPTION

Embodiments provide a method to assess the vulnerability of a person to noise-induced hearing loss, due to elevated environmental and or operational noise. This assessment is based on the identification of a functional biomarker for a reversible reduction in hearing sensitivity with exposure to noise, which indicates innate capacity for resistance to noise stress by the cochlea. In particular the amplitude and rate of change of the reversible reduction in hearing sensitivity within a short duration of noise exposure (for example within the first 1 to 20 minutes of noise exposure, preferably within the first 10 minutes) can be characterised to provide a measure of a subject's innate protection against or susceptibility to noise-induced hearing loss. This response may be easily and noninvasively measured via the functional biomarker identified by the inventors or less easily via measuring the auditory brainstem response (ABR). The biomarker is the reduction in a specific measure of the conversion of sound energy to active mechanical vibration in the cochlea known as the otoacoustic emission. In particular measuring the distortion product otoacoustic emission (DPOAE) enables direct measurement of the amplitude and rate of change of a subject's reversible reduction in hearing sensitivity with exposure to noise using straightforward test procedures and equipment.

An embodiment provides an audiometric test method where a noise stress test is applied to a subject, during the application of the noise stress test measuring one or more indicators reflecting a subject's purinergic adaptation to noise exposure and the measured indicators analysed to quantify degree of change and rate of change of the subject's purinergic hearing adaptation to noise exposure. An audiometric test system and audiometer configured to perform the test is also described below. The subject's purinergic hearing adaptation may be determined at the level of the cochlea or along the central auditory pathway. The test system can be configured to measure or record responses at one or more levels along the central auditory pathway, and the components included in the test system may vary depending on the different measurements at different levels. For example, otoacoustic emissions may be measured by a microphone, electrodes may be used to measure auditory brain stem response, spectral imaging, functional magnetic resonance imaging (fMRI) or magnetoencephalography (MEG) may also be used.

Studies have shown that sustained elevation in background sound leads to a progressive reduction in hearing sensitivity over approximately half an hour or less, which is sustained for many hours after return of sound to normal levels, due in large measure to release of ATP in the cochlea activating $P2X_2$ receptor ion channels. This purinergic hearing adaptation is otoprotective, as mice and people lacking these ion channels are more vulnerable to noise and age-related hearing loss. Recent studies by the inventors' (unpublished at the date of earliest filing) have discovered that the mechanism of action is the reduction in gain of the outer hair cell electromechanical transduction, which underlies the 'cochlear amplifier', evidenced by the exponential decay in outer hair cell-based distortion product otoacoustic emissions during noise in wild-type mice, which was not seen in mice null for the P2rx2 gene encoding $P2X_2$ receptor ion channels. The inventors' studies have identified that $P2X_2$ receptor-mediated hearing adaptation lies at the level of the outer hair cell-based cochlear amplifier. Reduction in gain of the outer hair cell electromechanical transduction (turning down the gain on the cochlear amplifier) is a biomarker for the $P2X_2$ receptor-mediated adaptation. Otoacoustic emissions can be used to directly measure the electromechanical transduction drive of the outer hair cells, and in embodiments this forms the basis for a test to indicate predisposition to noise-induced hearing loss. The inventors have also performed testing to confirm that DPOAE response provides a reliable measure of individuals' purinergic hearing adaptation. An indication of an individual's susceptibility to nose induced hearing loss can be determined from the individual's measured purinergic hearing adaptation response to an auditory stress test.

Embodiments provide an audiometric test method and audiometer for performing the test. The test comprises applying a noise stress test to a subject and during the application of the noise stress test measuring a subject's otoacoustic emissions. The measured otoacoustic emissions are analysed to quantify change in amplitude and rate of change of the otoacoustic emissions during noise exposure. The subject's reduction in noise sensitivity over the course of the noise stress test can be quantified based on the subject's otoacoustic emissions to output a measure indicative of the subject's vulnerability to noise-induced hearing loss. An embodiment is configured to measure a subject's DPOAE response, for example using an audiometer microphone to record the DPOAE. The measured DPOAE response is analysed to determine a measure indicative of the subject's vulnerability to noise-induced hearing loss.

An embodiment also provides a test method and test device for applying a noise stress test to a subject and during the application of the noise stress test measuring a subject's auditory brainstem response (ABR). ABR can be measured using either penetrating or surface electrodes. The ABR is analysed to quantify extent and rate of change during noise exposure. The subject's reduction in noise sensitivity over the course of the noise stress test can be quantified based on the subject's ABR to output a measure indicative of the subject's vulnerability to noise-induced hearing loss. Studies by the inventors have shown that ABR is an indirect measure of $P2X_2$ receptor-mediated adaptation and therefore an individual's innate susceptibility to noise-induced hearing loss. The analysis of ABR measurements may require signal filtering and averaging of results to reduce impact of non ABR related artefacts on the measurements.

The test may be of relatively short duration of noise presentation, for example 7 to 15 minutes. However, tests have shown that as little as 2-2.5 minutes noise exposure may be sufficient for adaptation to occur. This is due to the measure of the rate of change in adaptation being a key indicator of the natural $P2X_2$ receptor-mediated protection in the subject. This has an advantage of the test being able to be executed quickly. Further the short test duration reduces risk of any permanent hearing damage being caused by the test procedure itself.

Figure 1:
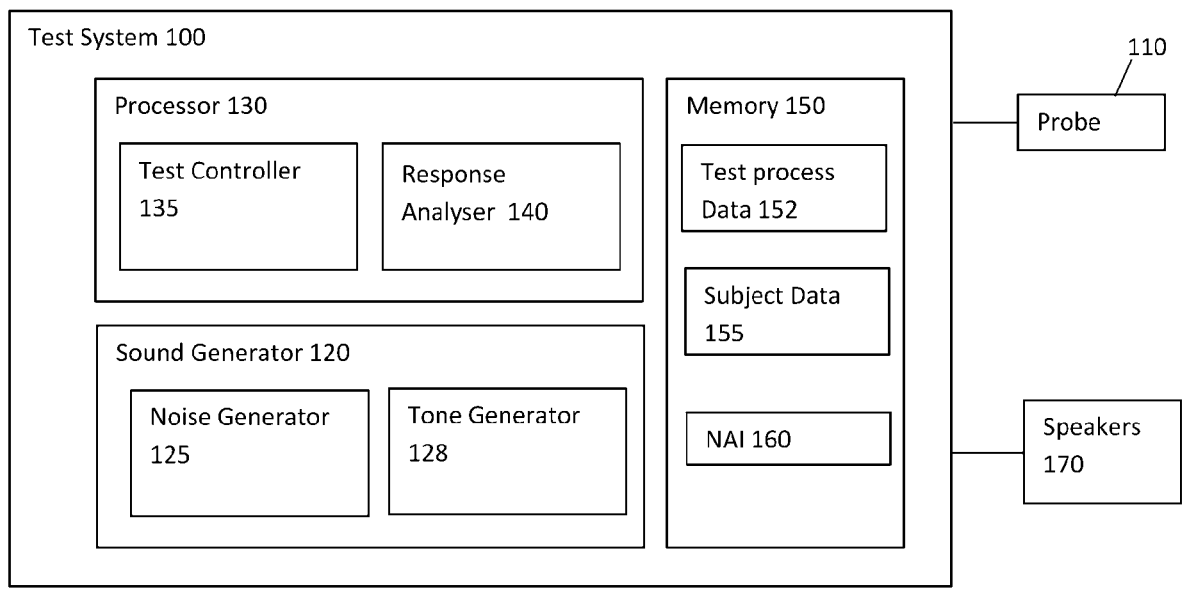
FIG. 1 is a block diagram of an embodiment of a test system.

An embodiment of a test system is illustrated in the block diagram of FIG. 1. The system 100 comprises a probe 110 configured for insertion into the external ear canal of a subject, a sound generator 120, and a processor 130 configured to control the test procedure and analyse measured response data. The probe 110 has a microphone (not shown) to detect DPOAE response to noise stimulus. The sound generator 120 configured to deliver noise stimulus to the subject in accordance with the test method. The sound generator may also be configured to deliver tones to stimulate a DPOAE response in some embodiments. The processor 130 is configured with a test controller 135 to automatically control the test to drive the sound generator 120 to deliver noise stimulus in accordance with an embodiment of the test method. This may include stopping noise delivery for measurement of the subjects DPOAE response, and generating two tones for DPOAE stimulus.

It should be appreciated that the test controller 135 may be implemented as a software module programmed to control execution of a defined test process 152, the executed test process may be one of a plurality of defined test processes 152 stored in system memory 150. The test controller may be configured to adjust test parameters based on feedback from the subject. For example, a test process may include a calibration phase to apply calibration stimulus and automatically detect onset of an OAE response, this threshold response level being used to feed into setting or adjusting pre-set test parameters, for example setting intensity levels for the two pure tones to be applied for eliciting the DPOAE response. The test process defines timing for application of noise and sampling the subject's response. Some test procedures may require temporarily halting noise application to take response measurements. However, some measurements may be made during noise exposure.

For example, a test method may include an initiation or calibration phase to determine subject specific response threshold and establish a baseline for test measurement (i.e. a baseline for DPOAE measurements). The test procedure defines periods for application of noise (and type of noise, for example white noise, pink noise, frequency ranges etc.) noise intensity levels in decibels and measurement timing. A flowchart of an example test procedure is shown in FIG. 18, a test procedure may define application of noise 1820 (for example for T=2.5 min), briefly interrupted for an OAE test where tones are delivered via speakers in the probe to stimulate an OAE response 1830 and the OAE response measured 1840 using a microphone, the test procedure can include several iterations of these steps—more noise (5 min), another test, then more noise (10 min) etc.—until completion of the test iterations 1850 and analysis of the results 1870. In this example testing is performed at set times however the measurement may be periodic, for example every two minutes from the onset of noise exposure to a defined finish time (i.e. 10-20 minutes). In an example where the subjects' response is measured as DPOAE the test uses two pure tones at different frequencies (f1 & f2) 1830 to stimulate the DPOAE response for measuring 1840. The f1 and f2 parameters can be matched to human hearing, for example around 4 kHz (f1 was 3.58 kHz, hence f2 was 4.48 kHz; but other frequencies may be used to show the same effect). In prototype testing embodiments, the inventors used asymmetric intensities for the levels of these two frequencies, where the intensity of f2 was set to 10 dB less than the intensity of f1. This test was performed at 3 different levels of f1 above threshold—55 dB SPL (sound pressure level), 60 dB SPL and 65 dB SPL. The relative intensity difference between the two tones f1 and f2 may vary between embodiments, for example the relative intensity different can be in the range of 0-30 dB. Although this example describes 3 iterations of noise application and testing, more or less may be used depending on embodiments and all variations are contemplated within the scope of the invention. Iterations of noise application and testing may be of different durations.

The subject's OAE response is detected by the probe microphone 110 and captured for analysis, for example, by using fast Fourier transformation to the frequency domain. Alternatively or additionally the system may include a sensor for measuring the subject's auditory brainstem response. A subject's OAE response may also be visually determined from the recordings, based on observation of the elicited response to sound stimulus around the threshold intensity range of probe tones. This observation may be performed by applying a sound signal having increasing intensity of probe tones and using a camera or other non-auditory pickup such as laser Doppler or ultrasonics to monitor for an elicited response within the outer, middle or inner ear. For example, the physical response can be movement of the tympanic membrane (ear drum). This is an alternative measurement method that may be applied additionally or alternatively to measuring OAE sound response using a microphone.

In some embodiments the analysis of the subject's measured response 155 to the noise stimulus may be performed by the system 100 to output a measure indicative of the subject's vulnerability to noise-induced hearing loss based on the subject's reduction in noise sensitivity over the course of the noise stress test. For example, a response analyser 140 may be implemented in the system controller 130 to quantify change in amplitude and rate of change of the response during noise exposure and assess the subject's response 155 against a noise adaptation index (NAI) 152.

The studies by the inventors have shown that a subject's reactive adaptation to applied noise within a short duration of the noise being applied is indicative of the subject's $P2X_2$ receptor-mediated hearing protection. This change may be measured based on OAE response or indirectly via monitoring and ABR response. Change in relative amplitude of response and rate of change in the initial period of noise exposure can be characterised using the test methods disclosed.

Using the test, a clinical evaluation of the variance of hearing adaptation across human populations may be performed, analysed and mapped to provide a Noise Adaptation Index. The Noise Adaptation Index (NAI) defining a scale of measurable parameters for application to objectively characterise a subject's $P2X_2$ receptor-mediated hearing adaptation, which may provide a measure indicative of the subject's vulnerability to noise-induced hearing loss.

In order to fully understand the nature of the present invention some explanation of the underlying research and discovery is provided in the following paragraphs, which aim to provide insight into the underlying physiology of hearing adaptation.

Sensory systems are characterised by adaptation processes that sustain transduction as stimulus intensity increases. The mammalian auditory system operates across an acoustic power range of ~120 dB, measured on the logarithmic decibel scale. The mechanism for the extraordinary acuity of the cochlea (recalling the age-old adage of "hearing a pin drop") arises from the commitment of 75% of the sensory hair cells, the outer hair cells, to electromechanical (reverse) transduction, driving a "cochlear amplifier". The nonlinear outer hair cell reverse transduction provides an ~40-dB gain at hearing threshold, reducing as sound levels rise. Studies by the inventors have investigated auditory physiology aiming to understand how hearing is preserved in the face of acoustic overstimulation, as noise can damage the cochlea and can greatly exacerbate hearing loss with aging.

Given the recent propensity for direct delivery of high-level recreational sound to the ear canals by personal music players and, more broadly, the impact on our hearing of noise from industrial and military environments, there is an imperative to better understand the intrinsic mechanisms that enable the cochlea to accommodate loud sound.

Known mechanisms by which the cochlea adjusts its sensitivity to loud sound include the middle-ear muscle reflex and efferent feedback to the outer hair cells. The middle-ear muscle reflex is largely driven by vocalization or intense low-frequency sound, and fatigues after a few minutes. Efferent neuronal adaptation is even more rapid (milliseconds to seconds) and provides dynamic modulation that enables the cochlea to unmask sounds of attentive interest from background noise. The olivocochlear efferent system is to some extent otoprotective against noise damage, and contributes to "conditioning", where sustained moderate sound exposure toughens the cochlea against subsequent acoustic overstimulation. However, this efferent feedback to the cochlea rapidly adapts at sound levels well below safe upper hearing limits (85 dB LAeq [equivalent continuous A-weighted sound pressure level (dB)]), as reflected in workplace legislation.

It has been shown that purinergic signalling contributes to cochlear adaptation to elevated sound levels and protection from overstimulation. A dominant-negative point mutation in the P2rx2 gene encoding the ATP-gated ion channel $P2X_2$ receptor subunit underlies the autosomal-dominant nonsyndromic progressive hearing loss locus DFNA41. DFNA41 stands for autosomal dominant nonsyndromic deafness-41. It is a locus on chromosome 12q24. This locus was discovered in a Chinese family to this particular part of the chromosome. A study including data using the $P2X_2$ receptor-encoding gene knockout (P2rx2-null) mouse model, demonstrated that noise exposure over a significant fraction of this animals' life caused progressive hearing loss starting at the higher hearing frequencies.

The $P2X_2$ receptor is abundantly expressed by cells lining the cochlear partition, including the sensory hair cells of the organ of Corti, Reissner's membrane epithelial cells, and spiral ganglion neurons. The cochlear partition maintains the positive endocochlear potential (EP; ~+100 mV) that, along with the negative membrane potential of the hair cells, provides the driving force for sound transduction. Both EP and the hair cell membrane potential are reduced by activation of $P2X_2$-like ATP-gated nonselective cation channels. Studies have shown that in the guinea pig cochlea, noise stress causes release of ATP into the K+-rich endolymphatic compartment, where $P2X_2$ receptors are concentrated. Thus, a role for ATP regulation of cochlear function via $P2X_2$ receptors is established at the cellular and tissue level. Evidence has also been provided showing that as the sound floor is elevated, ATP is released into the cochlear partition, activating $P2X_2$ receptors, which reduces sound transduction and synaptic transmission from the hair cells. This purinergic regulation of hearing sensitivity was revealed by the absence of auditory brainstem response (ABR) temporary threshold shift (TTS) in P2rx2-null mice. The mechanism is otoprotective, as P2rx2-null mice are highly vulnerable to noise-induced hearing loss with more extensive acoustic overstimulation.

These studies have associated susceptibility to noise-induced hearing loss (NIHL) with absence of the P2rx2 gene ($P2rx2^{(-/-)}$) encoding $P2X_2$ receptors. These studies have also shown that ATP-gated ion channels assembled from $P2X_2$ receptor subunits in the cochlea are necessary for the development of temporary threshold shift (TTS), evident in auditory brainstem response recordings as sound levels rise. In mice null for the P2rx2 gene (encoding the $P2X_2$ receptor subunit), sustained 85-dB noise failed to elicit the TTS that wild-type (WT) mice developed.

ATP released from the tissues of the cochlear partition with elevation of sound levels likely activates the broadly distributed $P2X_2$ receptors on epithelial cells lining the endolymphatic compartment. This purinergic signalling is supported by significantly greater noise-induced suppression of distortion product otoacoustic emissions derived from outer hair cell transduction and decreased suprathreshold auditory brainstem response input/out-put gain in WT mice compared with P2rx2-null mice. At higher sound levels (95 dB), additional processes dominated TTS, and P2rx2-null mice were more vulnerable than WT mice to permanent hearing loss due to hair cell synapse disruption. P2rx2-null mice lacked ATP-gated conductance across the cochlear partition, including loss of ATP-gated inward current in hair cells. These data indicate that a significant component of TTS represents $P2X_2$ receptor-dependent purinergic hearing adaptation that underpins the upper physiological range of hearing.

Put more simply, data from mouse studies of noise exposure-induced changes in measures of hearing function comparing wild type mice against a genetically engineered mouse lacking a specific ($P2X_2$) receptor, indicate that it is the $P2X_2$ receptor that drives protective desensitization of hearing. Thus, research by the inventors has demonstrated that loss of $P2X_2$ receptors makes mice (and people) vulnerable to noise-induced hearing loss (NIHL). However, while these studies showed that sustained noise caused cells in the cochlea to release ATP and this activates the $P2X_2$ receptor, these studies did not indicate where in the cochlea this was actually occurring.

Further studies by the inventors now indicate that the site of action is the cochlear outer hair cells. These outer hair cells are the mechanical amplifiers of the cochlea, transducing sound and converting that signal into amplified vibrations that are detected by the adjacent inner hair cells. Identifying the reduction in the amplitude of cubic DPOAE signal over time during noise presentation is the primary biomarker of the $P2X_2$ receptor-mediated hearing adaptation.

Further studies by the inventors sought improved resolution of the kinetics for the purinergic hearing adaptation and addressed whether the 'cochlear amplifier' derived from outer hair cell electromotility contributed to the $P2X_2R$-dependent reduction in neural output from the cochlea in the face of sustained noise exposure. To achieve this, rates of adaptation of hearing sensitivity with noise exposure were compared between wildtype mice and P2rx2(-/-) mice using ABR and outer hair cell-derived cubic distortion product otoacoustic emissions (DPOAE) measurements. The cochlear amplifier provides 40-60 dB gain of the sound energy driving transduction by the inner hair cells, that is coded at the type I spiral ganglion synapses. This outer hair cell electromechanical transduction can be directly measured by recording the evoked otoacoustic emissions that are generated by the interaction of sound-evoked cochlear amplifier micromechanics, derived from outer hair cell electromotility, with cochlear basilar membrane mechanics summating and reflecting vibrational energy back through the ossicular chain to the tympanic membrane and hence generating detectible sound in the ear canal.

Using two sound drivers enables detection via a microphone pickup in the ear canal, where the cubic (2f1−f2) DPOAE is prominent and reports the gain of the cochlear amplifier. Test data showed that the rate of purinergic hearing adaptation is considerably fast and stems from a reduction of cochlear amplifier gain.

In the inventor's studies using mice, male and female (9-17 weeks) wildtype ($P2rx2^{(+/+)}$) and P2rx2-null ($P2rx2^{(-/-)}$) mice on a C57Bl/6J background (Australian BioResources, Moss Vale, NSW, Australia) were used. Hearing testing was carried out in a sound-attenuating chamber using an auditory-evoked potential ABR and DPOAE workstation with signal processors programmed with software for performing the tests and signal analysis. Sound levels were calibrated using a one-quarter-inch free field calibration microphone. Electrostatic speakers, controlled by the workstation software, were used to evoke ABR potentials (16 kHz 5 ms tone pips; 0.5 ms rise/fall time, delivered at 10/sec) and to generate two primary tones of equal intensity (f1 and f2; f2/f1 ratio: 1.25 about 16 kHz) for the mouse DPOAE recordings. For ABR recordings, sub-dermal platinum needle electrodes were inserted at the vertex (+), over the mastoid process (−), and with a ground electrode in the hind flank. ABR potentials were amplified, filtered and averaged 512 times, with sound pressure levels (SPL) decreasing in 2.5 dB steps from 70 dB SPL to 10 dB SPL below threshold. The threshold level was defined as the intensity level where an ABR waveform above the noise floor (100 nV) could still be visually detected. The cubic (2f1−f2) DPOAEs [25] were detected using a microphone coupled to the ear canal, driven by the paired primary tones (168 ms duration, 6/sec from 0 to 70 dB in 2.5 dB SPL steps), with 50 sound stimuli analysed by Fast Fourier transformation. The threshold level for DPOAEs was defined as the sound level producing a cubic DPOAE with an amplitude of 5 dB above the noise floor. The noise floor was determined as an average of two points on either side of the cubic DPOAE.

The test method and apparatus disclosed herein enable practical measurement of the adaptation of cochlear outer hair cell function (the 'cochlear amplifier') in response to noise/sound presentation in humans on the precept that reduced hair cell function in a person is an indicator for risk of NIHL. It is an advantage of the disclosed test method that the test focuses on initial adaptation to noise, measuring the amplitude and rate of change, to allow assessment of the degree of an individual's protective response, which may be extrapolated to the effect of long term noise exposure. This test is performed within a time frame wherein the risk of any permanent damage by virtue of the test itself is minimised. Further by performing an initial calibration to determine the individual's threshold response level, the noise intensity required to validly measure the subject's response may also be set to reduce risk of permanent hearing damage (permanent threshold shift) being caused by the testing. Importantly the test method disclosed can provide a measure of the subject's susceptibility to noise-induced hearing loss before any actual damage has occurred.

In an embodiment, measurement of the adaptation of the cochlear hair cell function is achieved by measuring the decline of the cubic DPOAE during noise exposure, on the precept that people that show a reduced decline (akin to the lack of this $P2X_2$ receptor signalling in mice), would be at risk for NIHL.

This is based on the identification of a functional biomarker for a reversible reduction in hearing sensitivity with exposure to noise, which indicates innate capacity for resistance to noise stress by the cochlea. The biomarker is the reduction in a specific measure of the conversion of sound energy to active mechanical vibration in the cochlea known as the otoacoustic emission, and in particular, the distortion product otoacoustic emission (DPOAE).

People who demonstrate a significant decline in the amplitude of the DPOAE as the sustained level of background noise is raised above ambient levels, have a strong innate protection and will be resistant to noise stress. Conversely, individuals who exhibit significantly less than average reduction in the DPOAE with elevated noise are evidently vulnerable to irreversible noise-induced hearing loss (permanent hearing loss) and would benefit from more frequent monitoring of hearing to detect and hence limit progressive hearing loss.

The invention is the application of a functional test for dynamic, reversible reduction in DPOAE with elevated noise which can be matched to innate resistance/vulnerability to noise-induced hearing loss. This is based on the finding in an animal model(mouse) that noise-induced activation of a reversible reduction in DPOAE amplitude, elicited by a minimal elevation in background noise, reflects purinergic adaptation of the 'cochlear amplifier', that is noise-induced release of ATP from cochlear tissues, that acts upon the $P2X_2$ receptor type ATP-gated ion channels to reduce the sound-evoked electromechanical amplification of vibration in the sensori-epithelium (organ of Corti) of the cochlea generated by the outer hair cells.

Data from the inventors' studies with animal models demonstrates the specificity of the measurement of the time course for this purinergic ($P2X_2$ receptor specific) adaptation of the 'cochlear amplifier'—driven DPOAE, which represents a functional biomarker for innate resistance to hearing loss. In the mouse model, the presence of a $P2X_2$ receptor-mediated adaptation of DPOAE amplitude with a signature time constant of ~3 minutes, reflects normal resistance to noise-induced hearing loss. In the absence of this mechanism, mice and humans are susceptible to progressive hearing loss at medium rather than high sustained environmental noise exposures.

Embodiments of the current test are based on the finding in an animal model (mouse) that noise-induced activation of a reversible reduction in distortion product otoacoustic emissions (DPOAE) amplitude, elicited by a minimal elevation in background noise, reflects purinergic adaptation of the 'cochlear amplifier', that is noise-induced release of ATP from cochlear tissues, that acts upon the $P2X_2$ receptor type ATP-gated ion channels to reduce the sound-evoked electromechanical amplification of vibration in the sensori-epithelium (organ of Corti) of the cochlea generated by the outer hair cells.

The inventors' data obtained from mouse testing from animal models demonstrates the specificity of the measurement of the time course for this purinergic ($P2X_2$ receptor specific) adaptation of the 'cochlear amplifier'—driven DPOAE, which represents a functional biomarker for innate resistance to hearing loss. In the mouse model, the presence of a $P2X_2$ receptor-mediated adaptation of DPOAE amplitude with a signature time constant of ~3 minutes, reflects normal resistance to noise-induced hearing loss. In the absence of this mechanism, mice and humans are susceptible to progressive hearing loss at medium rather than high sustained environmental noise exposures.

The foundation for the diagnostic test for noise-induced adaptation of hearing sensitivity came out of studies of the changes in otoacoustic emissions in mice genetically manipulated to remove the $P2X_2$ receptor, which the inventors have previously shown to mediate the reversible reduction in hearing sensitivity with noise stress that provides endogenous protection to the cochlea. In the absence of this $P2X_2$ receptor, mice and people are vulnerable to noise-induced hearing loss. While it has been shown that sustained noise causes cells in the cochlea to release ATP and this activates the $P2X_2$ receptor, it was not known where in the cochlea this was actually occurring.

A new study (unpublished at filing date of the provisional application) by the inventors has shown that the site of action is the cochlear outer hair cells. These outer hair cells are the mechanical amplifiers of the cochlea, transducing sound and converting that signal into amplified vibrations that are detected by the adjacent inner hair cells. A small fraction of this amplified energy is reflected back out of the cochlea—through the ossicular chain (middle ear bones) to the ear drum, and can be detected as sound in the ear canal. Distortion product otoacoustic emissions are set up to measure sound transduction (such testing is similar to that used for newborn hearing screening) using two pure tones typically separated in a ratio of $f1=1.2 \times f2$ and the 'cubic' distortion product is mathematically predicted as $2f1-f2$; where f is the sound frequency. So, in effect, the test device can present two pure tones—say $f1=16$ kHz, then $f2=19.2$ kHz, to the ear canal and then use a microphone to measure the resultant cubic DPOAE which would be $2f1-f2=32-19.2=12.8$ kHz. So in effect, the test can collect sound from the external ear canal and record 3 sounds, the driving f1 and f2 sound used as the test stimulus and the cubic DPOAE at 12.8 kHz. It is the reduction in the amplitude of this cubic DPOAE signal over time during noise presentation that the inventors' most recent study shows is the primary biomarker of the $P2X_2$ receptor-mediated hearing adaptation.

Given that the inventor's earlier work has shown that loss of $P2X_2$ receptors makes mice and people vulnerable to noise-induced hearing loss (NIHL), the present test provides a practical method to measure and quantify that adaptation of cochlear outer hair cell function (the 'cochlear amplifier') with noise/sound presentation in humans, achieved by measuring the decline of the cubic DPOAE during noise exposure, on the precept that people that show a reduced decline (akin to the lack of this $P2X_2$ receptor signalling in mice), would be at risk for NIHL.

The inventors' key finding is that the decline in DPOAE with noise within a particular time frame (the majority of the adaptation of the signal occurs in the first 10 minutes) is a 'biomarker' for $P2X_2$ receptor-mediated hearing adaptation, and hence the strength of endogenous protection from NIHL (in the mouse model). Studies have now been extended to test human responses. In these latest experiments, the inventors used the same protocol and equipment as for our mouse studies—that is, baseline DPOAE measurements, and then noise (2.5 min), briefly interrupted for a DPOAE test, then more noise (5 min), another test, then more noise (10 min) etc. Stimulation frequency parameters f1 and f2 that were used were matched to human hearing around 4 kHz (f1 was 3.58 kHz, hence f2 was 4.48 kHz. Other frequencies are anticipated to show the same effect in alternative embodiments. In this test asymmetric intensities for the levels of these two frequencies were used, where the intensity of f2 was set to 10 dB less than the intensity of f1. This test was performed at 3 different levels of f1 above threshold—55 dB SPL (sound pressure level), 60 dB SPL and 65 dB SPL. For a subject exhibiting $P2X_2$ receptor-mediated adaptation to the applied noise, the measured OAE (or ABR) is expected to reduce, indicating "turning down" the gain on the cochlear amplifier. The magnitude and rate of change of the measured OAE or ABR provides a temporal profile of the subject's $P2X_2$ receptor-mediated adaptation response to the applied noise. This temporal profile characterising a subject's noise adaptation response can also be used to determine the degree to which the subject's hearing is protected by the response.

Different people will have different thresholds for OAE. It is therefore desirable to calibrate each test to the individual subject's AOE threshold, and set intensity levels based on this threshold—for example a given intensity level above the threshold (for example 10 dB). It should be noted that the use of asymmetric f1 and f2 intensity levels has previously been shown in previous studies to increase the sensitivity of detecting changes in DPOAEs with noise.

It should be noted that although previous studies have considered noise-induced hearing loss and the physiology of hearing protection, many of these studies concentrated on assessing post exposure hearing recovery. To the best of the inventor's knowledge, no one has previously systematically mapped the temporal profile for the progressive reduction in DPOAE with noise in people, and certainly the significance of that profile as a biomarker for the underlying purinergic hearing adaptation necessary to protect the cochlear from noise stress had not been previously identified.

It should also be noted that a subjects' auditory brain stem response (ABR) reflects both hair cell-based sound transduction (dominated by the outer hair cell—cochlear amplifier) and the synaptic transmission and compound action potential of the cochlear nerve and subsequent synchronous firing of the downstream central auditory nuclei—starting with the cochlear nucleus. The inventors have shown in their current (unpublished at filing and some sections incorporated in the research data below) mouse study that the ABR and DPOAE changes have a similar time courses for noise-induced reductions,—estimated as 3.0 minute time constant for the cubic DPOAE in mice (FIG. 15D), and for ABRs, the time constant was measured as 3.5 minutes (FIG. 16). The increase in threshold is largely complete within 10 mins (see FIG. 15B for the ABR threshold shift in the first 5 mins and 10 mins, and compare with FIG. 11A—the 4 blue dots on the left show that the shift is complete by 17.5 min and hence there was no significant difference at 37.5 min). So while ABR threshold shifts and changes in magnitude of the signal at a particular level over time with noise do show the $P2X_2$ receptor-mediated adaptation, the ABR is an indirect measure of the $P2X_2$ receptor-mediated adaptation (which is dominated by the outer hair cell—mediated change in electromechanical transduction). ABR measurements require a lot of signal averaging, whereas the response measurement can be faster and cleaner using the DPOAEs, which as noted are a specific measure of the effect on the upstream driver—namely the outer hair cell-derived 'cochlear amplifier'.

ABR as well as DPOAE measurements or instead of DPOAE measurements may be used to characterise a subject's $P2X_2$ receptor mediated adaptation, based on noting the magnitude of the changes in threshold over time. Threshold in either type of signals can be determined by changes in level of sound (driver) presented to the ear to first elicit a signal above the noise floor. Threshold can be determined visually, or using an algorithm with a set mean and variance above the noise floor. Visual threshold determination is based on identifying the point on the ABR evoked potential recordings where the sound-evoked signal can be visually discriminated as rising out of the noise floor at specific latencies from the start of the acoustic stimulus, reflecting synchronous action potential firing of groups of neurons within successive sites along the auditory brainstem pathway.

The ABR measurement of hearing function during the noise stress test may be used in conjunction with contemporaneous inclusion of otoacoustic emission measurements to provide an integrated measure of changing cochlear sound transduction and neurotransmission in response to the noise stress test.

In addition to determining the change in sensitivity—higher threshold means a louder driver sound level is required to seed the signal which is otherwise in the noise. In addition, it is possible to monitor the noise-induced hearing adaptation by using a constant driver sound level (above noise floor for the signal), and measure the reduction in the signal over time with noise presentation. Note for DPOAEs, the cubic (2f1–f2) has the strongest signal, but there are many other DPOAEs that could be measured as well—such as the quadratic (f2–f1).

Data from Human Studies

Hearing testing was carried out using an evoked potential and otoacoustic recording workstation (TDT system 3 with RX6 and RX6-2 signal processors, Tucker David Technologies, Ft Lauderdale, FL, USA) with BioSig32 software. The testing was performed using standard test hardware reprogrammed to be driven in accordance with the inventors' test method. While the DPOAE measurements were undertaken using this "off the shelf" equipment, the noise stimulus was generated by custom software and hardware, which for the human studies was used to drive a single channel of a calibrated headphone.

The cubic distortion product otoacoustic emissions (DPOAE at 2f1–f2) were recorded using a prototype system. The prototype system comprises a custom-made prototype ear canal probe coupled to a small microphone used to detect changes in sound pressure which represent DPOAEs, two sound generators and a controller. The sound generators can be electrostatic speakers, or moving coil magnetic speakers, or other types of sound transducers, either integrated into the probe for sounding directly in the ear canal, or external. In the prototype embodiment the controller was implemented by modifying a controller and software for an existing audiometric test, for example the TDT (Tucker David Technologies) system and the BioSigRP software. Two EC1 electrostatic speakers were controlled by the controller to generated unequal intensity primary tones (f1 and f1; f2/f1 ratio=1.25; L1=L2+10 dB). For human studies recordings were taken at 4 kHz presented from 50 to 65 dB SPL (in 5 dB increments). This was based on preliminary data in laboratory tests showing that a 4 kHz average probe frequency provided an optimum signal to noise ratio for the cubic DPOAE. This is also supported by previous, published noise exposure studies on humans. Furthermore, studies have also reported the importance of using unequal intensity primary tones for optimal cubic (2f1−f2) DPOAE sensitivity. Fifty measurements at 6.7 per second were averaged and analysed by Fast Fourier transformation. The DPOAE threshold for the human subject (n=1) was defined as the lowest sound level producing a cubic (2f1−f2) distortion product with an amplitude of 5 dB above the noise floor.

DPOAE measurements (minimum of three repeats per intensity) were recorded at baseline (pre-noise exposure) and immediately after each noise exposure. This allowed the investigators to track the development of the DPOAE (i.e. the reduction in amplitude over time). After the last noise exposure, the DPOAE was measured after 2.5 min, 7.5 min, 17.5 min, 37.5 min, 77.5 min, 157.5 min (and 187.5 min and 217.5 min for the 98 dB SPL noise exposure experiment; and 277.5 min for the 85 dB SPL noise exposure experiment) and 24 hours in order to track the recovery of the DPOAE.

Noise Exposure

Four noise levels (85 dB, 88 dB, 92 dB and 98 dB SPL; 2.5-4 kHz band width, white noise) were tested on different days and alternating between the left and the right ear. Sound levels were calibrated using a one-quarter-inch Free Field Measure Calibration Microphone (model 7016; ACO), and also confirmed using a Bruel & Kjaer audiometer (model 2250) with a ½ inch diffuse-field microphone (type 4942). The noise was delivered via headphones (Sennheiser HDA200) connected to custom noise generator software via a National Instruments interface. Cumulative noise presentation was for: 2.5 min, 7.5 min, 17.5 min and 27.5 min.

Data Analysis

Statistical analysis was performed using a paired, or unpaired, t-test (Sigmaplot®, Systat Software Inc.). Significance was determined as $p<0.05$.

Figure 2A:
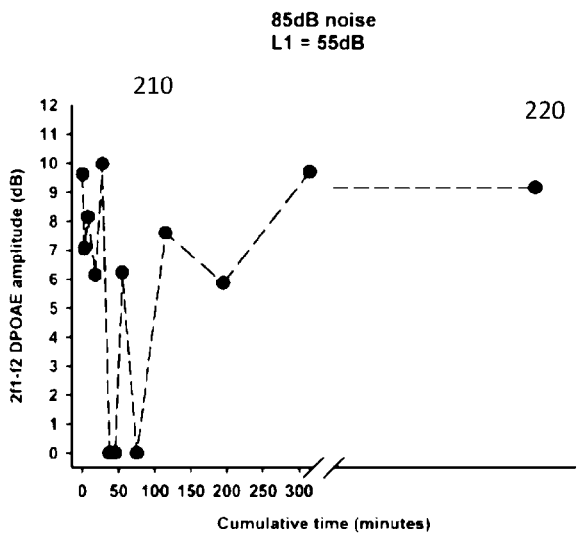
FIGS. 2a-c are graphs showing the reduction in cubic DPOAE (2f1–f2; around 4 kHz) with 85 dB SPL bandpass 2.5-4 kHz white noise in a human subject using varying probe intensity levels; noise stress test ran from 0 to 27.5 minutes, followed by recovery (last data point is at 24 hours).
Figure 2B:
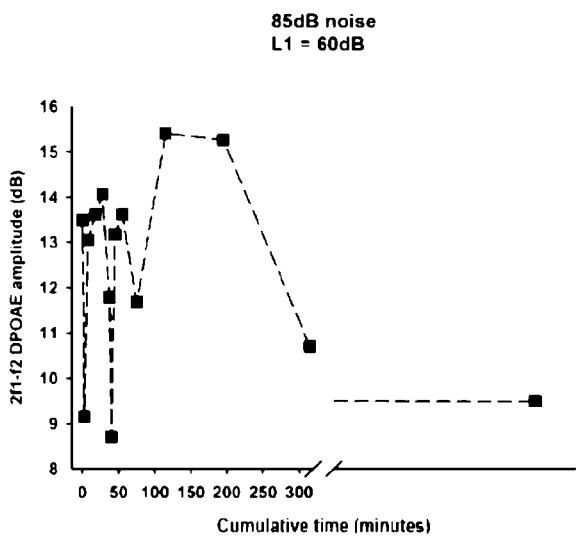
Figure 2C:
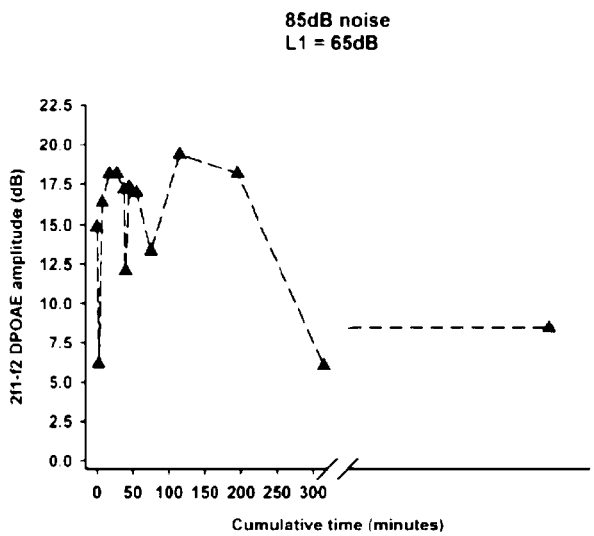

The graphs of FIGS. 2a-c show the reduction in cubic DPOAE (2f1−f2) with 85 dB SPL bandpass 2.5-4 kHz white noise in a human subject. This was measured around 4 kHz at three different levels (where L1 is for f1 and L2 is L1 −10 dB). The data for 55 dB SPL L1 show a reduction in DPOAE amplitude immediately after noise onset 210, which recovers fully by 24 hours 220. L1=60 dB SPL and L1=65 dB SPL show no sustained effect of noise. Noise was presented for 2.5 min, 5 min, 10 min, 10 min (cumulative total=27.5 min noise).

Figure 3A:
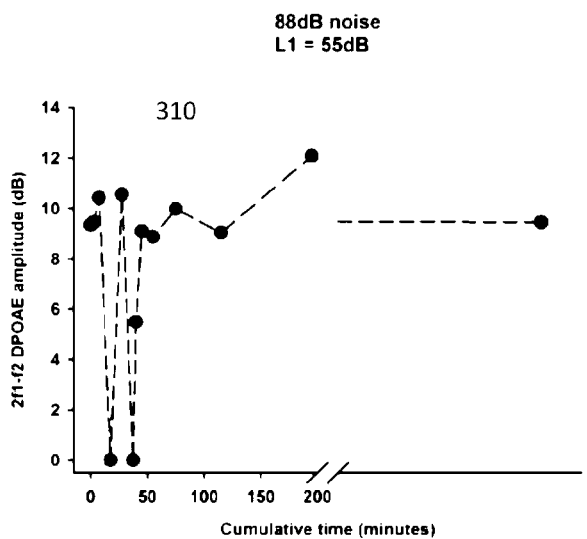
FIGS. 3a-c are graphs showing of reduction in cubic DPOAE (2f1–f2; around 4 kHz) with 88 dB SPL bandpass 2.5-4 kHz white noise in a human subject; noise stress test ran from 0 to 27.5 minutes, followed by recovery (last data point is at 24 hours).
Figure 3B:
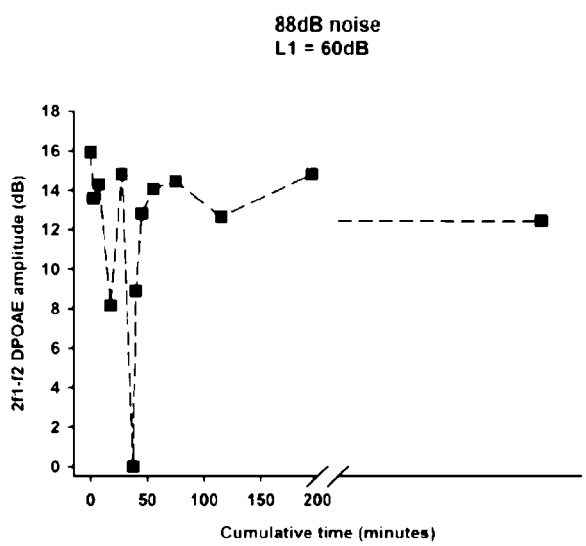
Figure 3C:
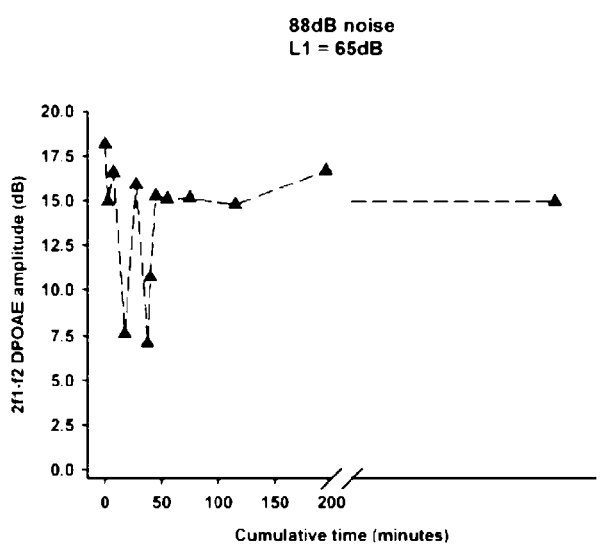

The graphs of FIGS. 3a-c show reduction in cubic DPOAE (2f1−f2) with 88 dB SPL bandpass 2.5-4 kHz white noise in a human subject, measured around 4 kHz at three different probe levels (where L1 is for f1 and L2 is L1 −10 dB). The data for 55 dB SPL L1 (FIG. 3a) showed a variable reduction in DPOAE amplitude with noise 310 which was also evident for L1=60 dB SPL, and L1=65 dB SPL. Noise was presented for 2.5 min, 5 min, 10 min, 10 min (cumulative total=27.5 min noise).

Figure 4A:
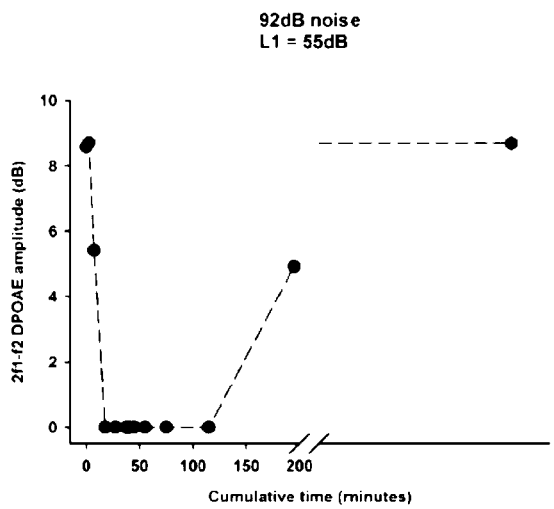
FIGS. 4a-c are graphs showing reduction in cubic DPOAE (2f1–f2; around 4 kHz) with 92 dB SPL bandpass 2.5-4 kHz white noise in a human subject; noise stress test ran from 0 to 27.5 minutes, followed by recovery (last data point is at 24 hours).
Figure 4B:
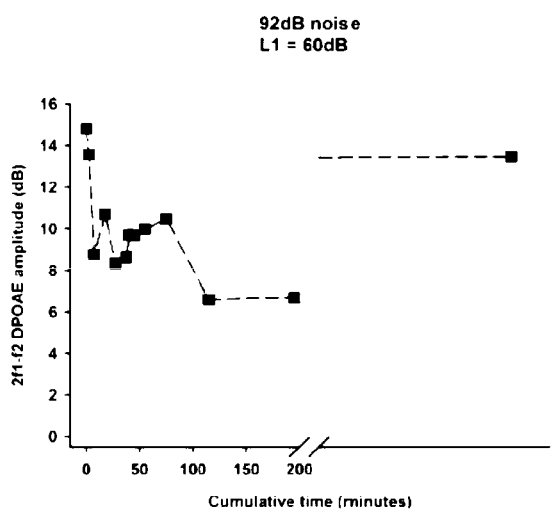
Figure 4C:
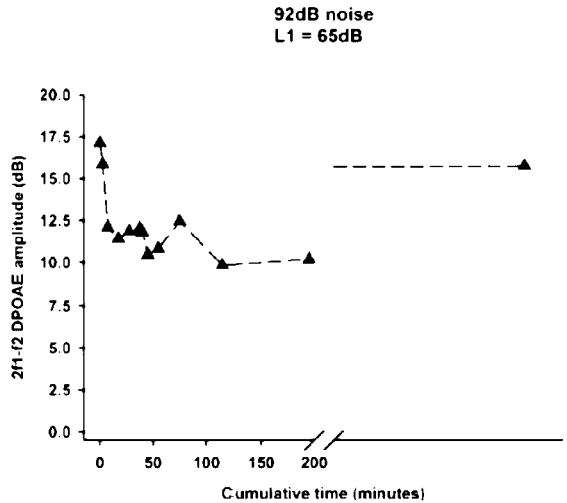

The graphs of FIGS. 4a-c show reduction in cubic DPOAE (2f1−f2) with 92 dB SPL bandpass 2.5-4 kHz white noise in a human subject, measured around 4 kHz at three different levels (where L1 is for f1 and L2 is L1−10 dB). The data for all three L1 probe levels 55, 60 and 65 dB SPL showed a progressive reduction in DPOAE evident from the first measurement at 2.5 minutes. This adaptation saturated within noise exposure period, and fully recovered by 24 hours. Noise was presented for 2.5 min, 5 min, 10 min, 10 min (cumulative total=27.5 min noise).

Figure 5A:
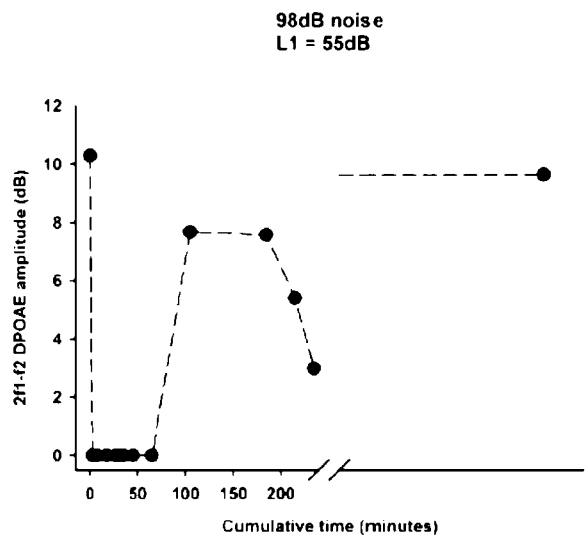
FIGS. 5a-c are graphs showing reduction in cubic DPOAE (2f1–f2; around 4 kHz) with 98 dB SPL bandpass 2.5-4 kHz white noise in a human subject; noise stress test ran from 0 to 27.5 minutes, followed by recovery (last data point is at 24 hours).
Figure 5B:
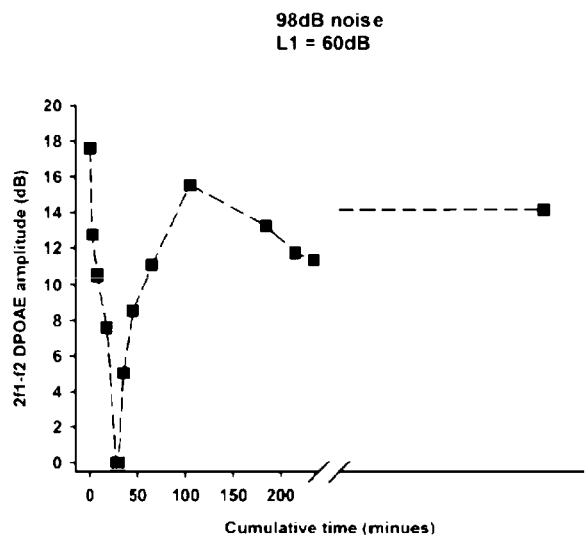
Figure 5C:
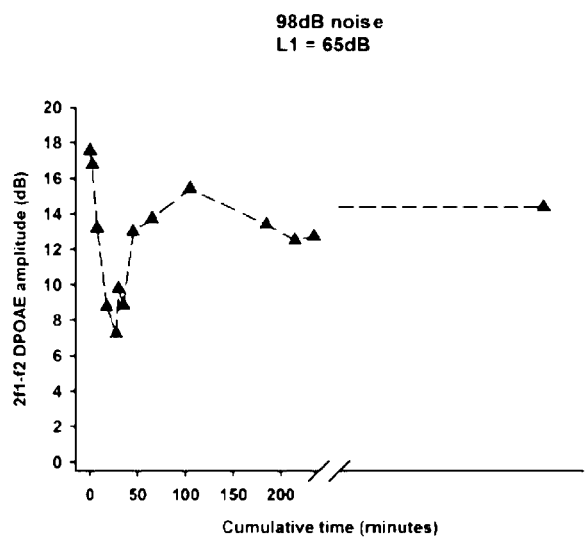

The graphs of FIG. 5a-c show reduction in cubic DPOAE (2f1−f2) with 98 dB SPL bandpass 2.5-4 kHz white noise in a human subject, measured around 4 kHz at three different levels (where L1 is for f1 and L2 is L1−10 dB). The data for all three probe intensity levels 55, 60 and 65 dB SPL showed a progressive reduction in DPOAE evident from the first measurement at 2.5 minutes. This adaptation saturated within noise exposure period, and fully recovered by 24 hours. Noise was presented for 2.5 min, 5 min, 10 min, 10 min (cumulative total=27.5 min noise).

Figure 6A:
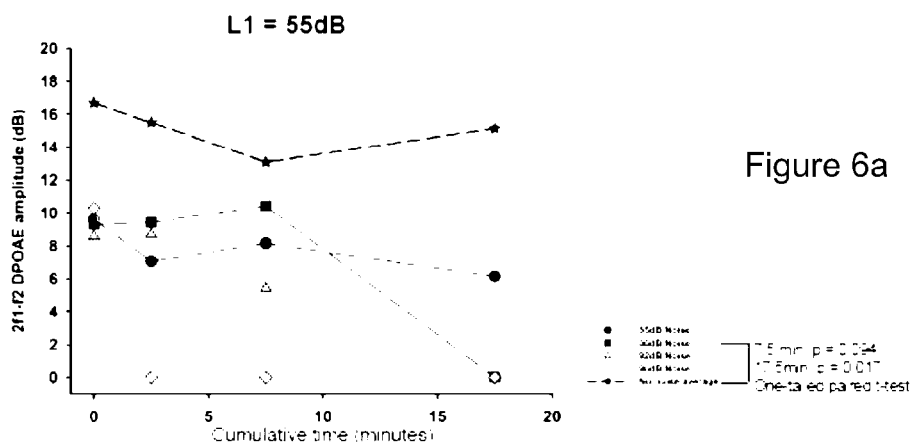
FIGS. 6a-c are graphs showing comparison of the temporal profiles for reduction in the cubic (2f1–f2; about 4 kHz) DPOAE signal during noise exposure (bandpass 2.5-4 kHz white noise) in a human subject; noise stress test ran during the time indicated, against a reference no-noise control.
Figure 6B:
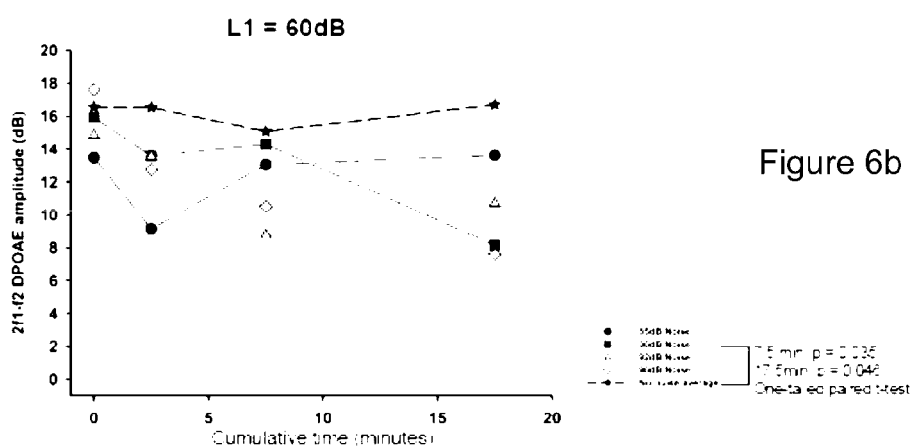
Figure 6C:
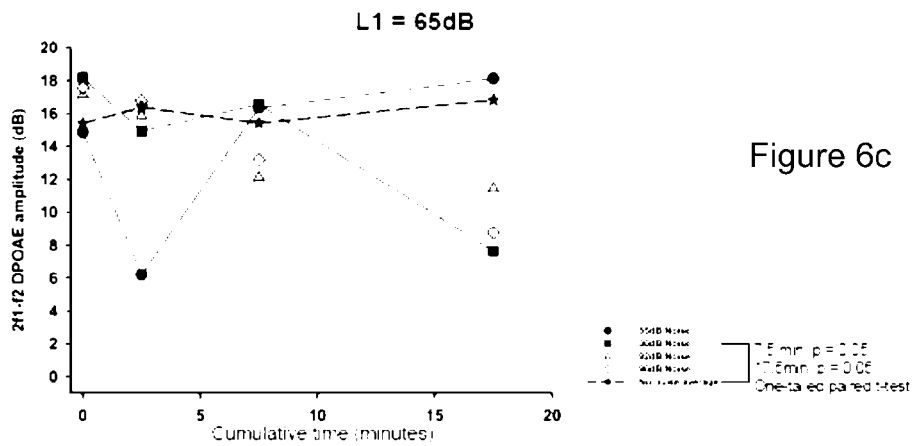

The graphs of FIGS. 6a-c show comparison of the temporal profiles for reduction in the cubic (2f1−f2) DPOAE signal during noise exposure in a human subject. Measurements were from either ear, with only one measurement made on an ear on any given day. The data resolve the sensitivity to the noise across the 85 dB SPL to 98 dB SPL test range (bandpass 2.5-4 kHz white noise). The no-noise (control) data is an average of 6 tests from two ears. Noise was presented for 2.5 min, 5 min, 10 min (cumulative total=17.5 min noise). Overall the majority of the adaptation in the DPOAE amplitude occurred within the first 7.5 min of noise.

The graph of FIG. 7 shows the least squares linear regression best-fits for the adaptation rate of the cubic (2f1−f2) DPOAE signal during noise exposure in a human subject at two noise levels (92 dB SPL and 98 dB SPL; bandpass 2.5-4 kHz white noise). Measurements were from either ear, with only one measurement made on an ear on any given day. The average rate at L1=60 dB SPL across the two noise levels was −0.853 dB/min. The average rate at L2=65 dB SPL for both noise intensities was 0.643 dB/min. The overall average noise-induced adaptation rate was 0.748±0.063 dB/min (mean±std. err. mean; n=4 measurements, across 92 & 98 dB SPL noise, combining the 60 dB SPL and 65 dB SPL L1 probe levels).

Indices of Noise-Induced Hearing Adaptation Measured from the Cubic DPOAE

Data from both the mouse study and the human study exhibit the following characteristics:

1. For a given probe level (L1), there is a decrease in the amplitude of the 2f1−f2 (cubic) DPOAE over time.
2. The time for this adaptation is comparable between mice and human with >50% of the change occurring within the first five minutes of noise exposure, and pseudo-steady state being achieved around 17.5 minutes of noise. The mouse study (discussed in example 1) used a 60 dB SPL L1 probe intensity=L2 to determine a 3.0 min time constant—from FIG. 15D. Here n=6 for wildtype mice and n=6 for the $P2X_2$ receptor knockout mice—where the data from the $P2X_2$ receptor knockout mice shows significantly less adaptation.

FIGS. 8 & 9 show linear regression best fit plots of this data set. The slope (rate) of noise-induced adaptation in the mouse cubic DPOAE—using 85 dB SPL noise and 60 dB SPL probes level (L1 and L2) is −1.117±0.276 dB/min for wildtype mice, and −0.654±0.09 for $P2X_2KO$ mice (mean±S.E.M); p=0.0258; unpaired t-test, two-tailed, n=6 per group. The (white) noise band for the mouse was 8-32 kHz; with f1 and f2 about 16 kHz.

FIG. 8 shows individual best fit linear regression plots of noise-induced adaptation of the cubic (2f1−f2) DPOAE in groups of wildtype and $P2X_2$ receptor knockout mice. The rate of adaptation determined as the average of the individual slopes for each group is significantly faster in wildtype mice, than those lacking expression of the $P2X_2$ receptor ($P2X_2R$ knockout); mean=−1.117±0.276 dB/min and −0.654±0.09 dB/min, respectively; p=0.0258; unpaired t-test, two-tailed, n=6 per group. The (white) noise band was 8-32 kHz; with f1 and f2 about 16 kHz driving the DPOAEs.

FIG. 9 shows average best fit linear regression plots of noise-induced adaptation of the cubic (2f1–f2) DPOAE in groups of wildtype and $P2X_2$ receptor knockout mice. The rate of adaptation is faster in wildtype mice, than those lacking expression of the $P2X_2$ receptor ($P2X_2R$ knockout); −1.117 dB/min and −0.654 dB/min, respectively; n=6 per group. The (white) noise band was 8-32 kHz; with f1 and f2 about 16 kHz driving the DPOAEs.

The human study used three different probe levels L1=55 dB SPL, L1=60 dB SPL and L1=65 dB SPL; with L2 being 10 dB less than L1. This study also used four different noise intensity levels (85 dB SPL, 88 dB SPL, 92 dB SPL and 98 dB SPL; 2.5 kHz-4 kHz bandpass white noise, with f1 and f2 about 4 kHz. These human data showed that the noise-induced adaptation would be robustly detected across all three probe levels at 92 dB SPL and 98 dB SPL, and could be detected at the lower probe levels with lower noise levels. Note that the 55 dB SPL probe level was the first practical level to test the subject (probing the 4 kHz region of hearing), as the DPOAE was not detectable at 50 dB SPL=L1 at this frequency in this individual; i.e. the DPOAE was masked by the noise-floor. The rate of adaptation appeared faster using the L1 probe at 60 dB SPL than when L1 was 65 dB SPL, across both the 92 dB SPL and 98 dB SPL noise intensities.

It should be noted that 3 dB is a doubling/halving of intensity; dB SPL is an absolute measure of this logarithmic scale where SPL stands for sound pressure level—set to 1 Pascal (1 Pa)=94 dB SPL.

The inventors have identified a means to assess the vulnerability of a person to noise-induced hearing loss due to elevated environmental/operational noise. This is based on the identification of a functional biomarker for a reversible reduction in hearing sensitivity with exposure to noise that indicates innate capacity for resistance to noise stress by the cochlea. The biomarker is the reduction in a specific measure of the conversion of sound energy to active mechanical vibration in the cochlea known as the otoacoustic emission, and in particular, the distortion product otoacoustic emission (DPOAE). This test has potential commercial value as the first practical predictor of vulnerability to workplace-induced hearing injury. For example, this assessment could become a de-facto standard practice in many noise-intense industries—particularly the military, heavy industry and airlines.

People who demonstrate a significant decline in the amplitude of the DPOAE as the sustained level of background noise is raised above ambient levels, have a strong innate protection and will be resistant to noise stress. Conversely, individuals who exhibit significantly less than average reduction in the DPOAE with elevated noise, are evidently vulnerable to irreversible noise-induced hearing loss (permanent hearing loss). Such individuals would benefit from more frequent monitoring of hearing to detect and hence limit progressive hearing loss. Such individuals may also choose to take additional measures to protect their hearing, such as avoiding high noise environments, frequent use of hearing protection, choosing high quality hearing protection, etc.

The invention is the application of a functional test for dynamic, reversible reduction in DPOAE with elevated noise which can be matched to innate resistance/vulnerability to noise-induced hearing loss. This is based on the finding in an animal model(mouse) that noise-induced activation of a reversible reduction in DPOAE amplitude, elicited by a minimal elevation in background noise above the intensity of the test sounds used to elicit the DPOAE, reflects purinergic adaptation of the 'cochlear amplifier', that is noise-induced release of ATP from cochlear tissues, that acts upon the $P2X_2$ receptor type ATP-gated ion channels to reduce the sound-evoked electromechanical amplification of vibration in the sensori-epithelium (organ of Corti) of the cochlea generated by the outer hair cells.

The inventors have shown that the change in (cubic) DPOAE over the first 10 minutes of noise exposure is largely due to $P2X_2$ receptor—mediated hearing adaptation—because that is proven in the mouse study (for a particular noise level), and the human study has the same characteristics across a practical level of noise exposure.

This is reflected as being able to measure the reduction in the DPOAE at different time points to quantify both the overall change in amplitude, and the rate of that change (change/time). That rate may vary with probe level but the test needs to be run at a level where the noise-induced adaptation does not push the DPOAE into the noise. The inventors' studies have shown 60 dB SPL and 65 dB SPL probe levels to be effective. So if a human subject had a threshold at the 4 kHz test frequency of 40 dB, then it is likely that 50 dB and 55 dB SPL L1 probe intensities would provide comparable data. Characterisation of the noise-induced hearing adaptation in some embodiments can test and assess responses across multiple test frequencies.

An embodiment of the test involves establishing the DPOAE threshold (at a particular frequency). This detection of the subject threshold may be performed by stepping up probe L1/L2 intensities and measuring to determine where a DPOAE response is first measurable—the threshold. The test then running at threshold+10 dB for L1, where L2=L1−10 dB. It should be appreciated that this is one example and other ratios of L1 and L2 may be used. For example, mouse studies have shown that L1=L2 would work, as well as other ratios. Baseline measurement of the cubic DPOAE is then made, followed by presentation of noise. In an embodiment the noise will be presented around 92 dB SPL—but this may vary between embodiments. The duration of the noise presentation is around 10 minutes with measurement of the DPOAE. The duration of the test may be longer or shorter than 10 minutes, for example 5 to 15 minutes. In some embodiments the DPOAE measurements may require brief interruptions in the noise exposure, and in such embodiments the noise time would be cumulative. Whether or not noise presentation is halted for DPOAE measurement may depend on the audiometric equipment being used for measuring the DPOAE.

It should be noted that the safe maximum daily noise dose is 85 dB Level A for 8 hours, 88 dB level A for 4 hours, and 91 dB Level A for 2 hours, and 94 dB for 1 hour. Thus, some embodiments may utilize 91 dB Level A noise which provides a good safety margin for a 10 minute noise exposure hearing test.

Although the above embodiments are discussed using DPOAE and ABR response measures in detail. Other indicators of purinergic hearing adaptation can be used. For example, in an embodiment, the measure of change in cochlear function during the noise stress test may be determined indirectly by measuring altered auditory-related brain function. Such auditory-related brain function may be determined using electrophysiological measurements, such as with auditory brainstem responses (ABR).

In another embodiment, hearing adaptation in response to a noise stress test may be recorded using spectral imaging of markers of brain activity, where such imaging may utilise excitation and emission across the expanse of the electromagnetic spectrum. Examples of this may include, and are not exclusive to the use of infrared spectral imaging of regional brain oxygenation dynamics related to acoustic stimulation, functional magnetic resonance imaging (fMRI) or magnetoencephalography (MEG)—imaging of auditory brain function.

An aspect involves development of a Noise Adaptation Index (NAI). The NAI is developed based on clinical evaluation of the variance of hearing adaptation across human populations. Measurements of the dynamic range of adaptation over time can be used as parameters for developing a Noise Adaptation Index (NAI). For example, but not limited to this formula, the data from the 92 dB SPL noise with 60 dB SPL L1 probe intensity could be used to determine a NAI as the absolute value of the slope of the linear regression—which is 0.828 (dB/min) (see FIG. 6 above). By comparison, from mouse data, the NAI was on average 1.117 (dB/min) (new data, n=6), as compared to the $P2X_2$ knockout mouse where the NAI was 0.654 (dB/min) (no purinergic hearing adaptation). Once a human normal reference set of data is acquired, individual NAIs would be compared with the population distribution and extrapolating from the mouse data, individuals whose binaural average (testing both ears) fell in the bottom 25% of the NAI index range would appear likely to be classed as vulnerable to progressive hearing loss from noise stress. In the future, it may be possible to apply this test to a group of people known to have a natural loss of function mutation in the $P2X_2$ receptor gene, and these data would establish the lower boundary for purinergic hearing adaptation.

Alternative measurements of a NAI may be determined by calculation of surface areas of best fits for multiple probe level measurements across time. In addition, multiple probe frequencies could be determined using DPOAE measurements.

An embodiment of the invention provides an NAI audiometer (preferably handheld or portable with a handheld probe) that includes the data for the population NAI distribution. The NAI audiometer can be configured to perform testing of a subject as described above and to automatically compare the test data with that data file to provide a readout in terms of NAI and relative noise-induced hearing loss vulnerability. This may include outputting a position within that population distribution (percentile above adaptation floor) for the subject. The NAI may be offset by data from human subjects lacking $P2X_2$ receptor-mediated adaptation to noise, to set a zero baseline.

A NAI audiometer may include the DPOAE probe which would be inserted into the ear, noise would be delivered through the probe, and DPOAE changes measured across multiple probe frequencies and levels (this may be during a brief interruption of the noise). The noise could be random/white noise, Gaussian noise, or even particular pure tones or combinations of pure tones, clicks or a combination of samples sounds of natural or synthetic origin. It should be appreciated that the noise used during the testing may be any one or combinations of these different noise variants.

In an embodiment the NAI audiometer may be implemented as a virtual instrument, where a testing algorithm may be customized to suit pre-existing clinical audiology workstations. The NAI may be integrated into a range of DPOAE analysis—where changes in signal evident within the first tens of minutes of noise exposure provide the basis for the NAI. The NAI audiometry system may also incorporate auditory brainstem response (ABR) measurements either complementary to, or instead of the DPOAE measurements. The NAI audiometry system may also use additional signal modalities, not limited to extension to MEG, fMRI, or functional optical imaging signals related to auditory sound transduction and auditory neurotransmission arising from the cochlea.

In an embodiment the NAI further includes characterisation of the rate of recovery from the 'noise stress test' which may provide additional information regarding a subject's protective adaptation response. The $P2X_2$ receptor-mediated hearing adaptation resets very slowly—in mice, it has a time constant of about 12 hours, based on ABR measurements. However, in humans it appears more complicated. Pilot studies by the inventors showed some recovery over several hours (see FIGS. 2-5), with full recovery the next day (24 hours). In one example the test method may include a follow-up measurement an hour after the initial (2.5-15 minute noise test) to offset the change by the return in signal over that initial period. The characterisation of recovery parameters may be refined based on clinical trials and in particular in light of testing individuals who don't possess normal functioning $P2X_2$ receptors.

An embodiment includes both audiometric population weightings determining the significance of an individual's adaptive response to the noise stress with regard to vulnerability to noise-induced hearing loss, alongside a weighting for the personalized genetic or transcriptomic profile of the individual with regard to genetic variability screens impacting on hearing loss.

Embodiments test for a biomarker for susceptibility to workplace hearing injury. This test could become an industry standard (under license) as a specific hearing test to enable screening of employees who are likely to be vulnerable to noise-induced hearing loss due to high sound levels in the workplace. The license could be issued to a specific manufacturer of the test equipment—for measuring otoacoustic emissions in the audiology clinic or in mobile testing.

This has commercial value as the first practical predictor of vulnerability to workplace induced hearing injury. This assessment would necessarily become a defacto standard practice in many noise-intense industries—particularly the military, heavy industry and airlines.

Research Data from Mouse Studies:
Hearing Function Tests

Hearing testing was carried out in a sound-attenuating chamber using an auditory-evoked potential and DPOAE workstation (TDT system 3 with RX6 and RX6-2 signal processors, Tucker Davis Technologies, Ft Lauderdale, FL, USA) with BioSig32 software. Sound levels were calibrated using a one-quarter-inch free field calibration microphone. The mice were anaesthetised with either isoflurane, or a cocktail of ketamine/xylazine/ketamine(K/X/A).

Electrostatic speakers controlled by the TDT system using BioSigRP software were used to evoke ABR potentials (16 kHz 5 ms tone pips; 0.5 ms rise/fall time, delivered at 10/sec) and to generate two primary tones of equal intensity (f1 and f2; f2/f1 ratio: 1.25 about 16 kHz) for DPOAE measurements.

For ABR recordings, sub-dermal platinum needle electrodes were inserted at the vertex (+), over the mastoid process (−), and with a ground electrode in the hind flank. ABR potentials were amplified, filtered and averaged 512 times, with sound pressure levels (SPL) decreasing in 5 or 2.5 dB steps from 70 dB SPL to 10 dB SPL below threshold. The threshold level was defined as the intensity level where an ABR waveform above the noise floor (±100 nV) could still be visually detected. The growth function of the ABR was determined by off-line analysis of the N1–P2 wave amplitude.

The cubic (2f1–f2) DPOAEs were detected using a small microphone (ER-B10+, Etymotic Research, IL, USA) coupled to the ear canal in response to the paired primary tones (168 ms duration, 6/sec from 0 to 70 dB in 5 dB SPL steps (Study 1) or 2.5 dB SPL steps (Study 2)). In study 3, the DPOAE was measured at the 60 dB SPL input level. A total of 50 sound stimuli (Studies 1 and 2) per sound level, or 25 sound stimuli for the 60 dB SPL sound level (Study 3) were analysed by Fast Fourier transformation. The threshold level for DPOAEs was defined as the sound level producing a cubic DPOAE with an amplitude of 5 dB above the noise floor.

Noise Exposure

Broadband white noise (8-32 kHz for Studies 1 and 2; 9-32 kHz for Study 3) with an intensity of 85 dB SPL was created using custom software to generate the sound signal which was delivered using a D-A converter driving a speaker via an amplifier.

Hearing function tests (ABR and DPOAE) were measured before noise exposure (t0), and at a series of time points after cumulative noise exposure in three complementary studies; Study 1: 7.5 minutes (t7.5), 17.5 minutes (t17.5) and 37.5 minutes (t37.5), (k/x/a anaesthesia; ABR & DPOAE); Study 2: 7.5 minutes (t7.5) and 17.5 minutes (t17.5), (isoflurane anaesthesia; DPOAE); Study 3: 2.5 minutes (t2.5), 5 minutes (t5) and 7.5 minutes (t7.5), (isoflurane anaesthesia; DPOAE) or 5 minutes (t5) and 10 minutes (t10), (k/x/a anaesthesia; ABR). The opposite ear of the same mouse receiving noise treatment was used for no-noise treatment (silent) controls for ABR and DPOAE measurements (Studies 1 & 2), at least three days prior to, or after, the noise exposure experiment. In Study 3, different mice were used for the DPOAE and the ABR measurements. K/x/a anaesthesia is an abbreviation for an anaesthetic cocktail of ketamine, xylazine and acepromazine, delivered via intraperitoneal injection.

Data Analysis

Data are presented as the population mean±S.E.M. Statistical analysis was performed using one-way repeated measures Analysis of Variance (ANOVA), two-way repeated measures ANOVA and one-sample t test as indicated in Tables 1-7. Data were tested for normal distribution and Holm-Sidak post hoc analysis was utilised for multiple pairwise comparisons within ANOVA.

Results: Purinergic Hearing Adaptation Measured by ABR Across 7.5-37.5 Minutes Noise A first study (Study 1) validated the ABR TTS profile with noise exposure in $P2rx2^{(+/+)}$ mice and confirmed the absence of this purinergic hearing adaptation in $P2rx2^{(-/-)}$ mice alongside unexposed controls for both genotypes (littermates) to assure stability of hearing function during K/X/A anaesthesia. ABR measurements were obtained using 16 kHz tone pips undertaken before and during exposure to 85 dB SPL cumulative noise of 7.5 minutes (t7.5), 17.5 minutes (t17.5) and 37.5 minutes (t37.5) for $P2rx2^{(+/+)}$ and $P2rx2^{(-/-)}$ mice. These mice were also tested across these time intervals with mock presentation of noise (silent control groups; opposite ear) on a different day to control for the effect of the k/x/a anaesthesia. FIG. 10a shows examples of ABR recordings at baseline (i.e. before noise exposure) and after a cumulative noise exposure of 17.5 minutes, where an increase in threshold is apparent for the $P2rx2^{(+/+)}$ mouse but not the $P2rx2^{(-/-)}$ mouse. The threshold shift was fully reversible, established by re-measurement 24-96 hours post-noise.

FIG. 10a, shows examples of ABR traces before (baseline) and after 17.5 minutes cumulative noise exposure (post-noise). The hearing threshold in the $P2rx2^{(+/+)}$ mouse increased from 0 dB SPL 1010 to 7.5 dB SPL 1020 (blue dashed lines), whereas in the $P2rx2^{(-/-)}$ mouse, threshold remained unchanged at 2.5 dB SPL 1030, 1040 (red dashed lines).

The data from the noise exposure of the $P2rx2^{(+/+)}$ and $P2rx2^{(-/-)}$ groups is shown in FIG. 10b, where there was significant TTS in the $P2rx2^{(+/+)}$ mice by 7.5 minutes ($P2rx2^{(+/+)}$ vs. $P2rx2^{(-/-)}$: 5.2±0.6 dB vs. 1.25±1.1 dB respectively; p<0.001; n=12 and n=10; two-way RM ANOVA). This was maintained at 17.5 minutes cumulative noise ($P2rx2^{(+/+)}$ vs. $P2rx2^{(-/-)}$: 7.9±1.1 dB vs. 3.8±0.9 dB respectively; p=0.004; n=12 and n=10; two-way RM ANOVA) and at 37.5 minutes noise ($P2rx2^{(+/+)}$ vs. $P2rx2^{(-/-)}$: 10.0±1.7 dB vs. 4.4±1.5 dB respectively; p=0.002; n=11 and n=9; two-way RM ANOVA). These data indicated that the majority of the TTS (purinergic adaptation) occurred within this initial 7.5 minutes of noise exposure. The significant differences between noise-exposed ears and the unexposed control ears in these $P2rx2^{(+/+)}$ mice show that the TTS development is due to the noise ($P2rx2^{(+/+)}$, t7.5, t17.5, t37.5 p<0.001 for each time point; n=11-12, $P2rx2^{(+/+)}$ no-noise control, n=11; two-way RM ANOVA; FIG. 10b, Table 1), and not due to non-noise-related reduction in hearing sensitivity, such as prolonged anaesthesia. As evident from these data, the $P2rx2^{(-/-)}$ mice showed no significant ABR threshold shift with noise over the study period (p=0.134, n=9-10; two-way RM ANOVA). This was further established by comparing the noise-exposed against unexposed ears for these $P2rx2^{(-/-)}$ mice, which showed no significant difference at any time point (t7.5, p=0.998; t17.5, p=0.081; t37.5, p=0.992; n=9-10, P2rx2(-/-), n=9, control; two-way RM ANOVA; FIG. 10b, Table 1); where again, baseline hearing sensitivity was maintained in the absence of noise exposure. Overall, this validated the $P2X_2R$-mediated hearing adaptation model and also revealed that when hearing sensitivity baseline was stable, the noise-induced hearing adaptation developed within the first 7.5 minutes of cumulative noise exposure.

N1–P2 amplitude of the ABR record for the $P2rx2^{(+/+)}$ mouse post-nose is shown in the upper right trace (60 dB SPL stimulus, 1.2 µV output), such ABR measurements were used for input/output analysis (see FIG. 11). FIG. 10b shows, boxplots with data overlay (open circles) of the ABR threshold shifts after 7.5 minutes, 17.5 minutes and 37.5 minutes cumulative noise exposures (filled boxes), or no-noise (silent) controls (diagonally striped boxes) assessed using a 16 kHz tone pip stimulus (P2rx2(+/+), n=11; $P2rx2^{(-/-)}$, n=9). The ABR threshold shift was significantly different between $P2rx2^{(+/+)}$ (filled blue box) and $P2rx2^{(-/-)}$ (filled red spotted box) mice at all time points (t7.5, P=0.008; t17.5, P=0.009; t37.5, P<0.001). Dashed lines show the mean; solid lines show the median. Error bars represent the 95th percentile. See Table 1 for a more comprehensive statistical analysis.

TABLE 1

16 kHz ABR threshold shifts for Study 1.
16 kHz ABR threshold shifts

| | Treatment | | | | | | |
|---|---|---|---|---|---|---|---|
| | Silent vs. Noise | Silent vs. Noise | Silent | Noise | | Noise | Noise |
| | | | | Genotype | | | |
| Time point | $P2rx2^{(+/+)}$ | $P2rx2^{(-/-)}$ | $P2rx2^{(+/+)}$ vs. $P2rx2^{(-/-)}$ | $P2rx2^{(+/+)}$ vs. $P2rx2^{(-/-)}$ | Time point | $P2rx2^{(+/+)}$ | $P2rx2^{(-/-)}$ |
| t7.5 | <0.001 | .999 (n.s.) | 0.432 (n.s.) | <0.001 | t7.5 vs. t17.5 | 0.366 (n.s.) | 0.12 (n.s.) |
| t17.5 | <0.001 | 0.09 (n.s.) | 0.701 (n.s.) | 0.004 | t17.5 vs. t37.5 | 0.783 (n.s.) | 0.993 (n.s.) |
| t37.5 | <0.001 | 0.992 (n.s.) | 0.07 (n.s.) | 0.002 | | | |

As previously established, the $P2rx2^{(-/-)}$ mice showed no threshold shift (FIGS. 10a-b) and these data across the time intervals were not significantly different from the silent control measurements of both genotypes ($P2rx2^{(+/+)}$ or $P2rx2^{(-/-)}$ (FIG. 10b; Table 1; two-way repeated measures ANOVA; one sample t tests for threshold differences from zero; p>0.05). In contrast, there was significant TTS attributable to purinergic adaptation of the ABR thresholds in the $P2rx2^{(+/+)}$ mice by 7.5 minutes (5.00±0.58 dB) and this increased to 9.77±1.56 dB by the 37.5 minutes end-point (FIG. 10b).

The N1-P2 peak amplitudes of the ABR wave (see feature in FIG. 10a, $P2rx2^{(+/+)}$, 60 dB SPL post-noise ABR trace) allowed determination of cochlear nerve fibre recruitment with increasing tone pip stimulus intensity. This measured hearing function beyond threshold, where there is recruitment of type I spiral ganglion nerve fibres which have higher firing thresholds and different firing rates (FIGS. 11A, B). FIG. 11 shows ABR input/output (I/O) growth functions and gain for $P2rx2^{(+/+)}$ and $P2rx2^{(-/-)}$ mice based on the amplitude of the N1-P2 wave (indicated in FIG. 10a). Plot A of FIG. 11, demonstrates that $P2rx2^{(+/+)}$ mice show a reduction in slope over time (t0 vs. t37.5 measured between 30 and 50 dB SPL, P=0.003; n=11), while the slope in $P2rx2^{(-/-)}$ mice is unchanged over time, shown in plot B of FIG. 11 (t0 vs. t37.5 measured between 30 and 50 dB SPL; P=0.607; n=9). Plot C of FIG. 11 shows the ABR I/O gain (measured between 30-50 dB SPL intensity) in $P2rx2^{(+/+)}$ mice show a significant change over time (t0 vs. t37.5, P=0.002; n=11; filled blue boxes) in contrast to the $P2rx2^{(-/-)}$ mice (t0 vs. t37.5, P=0.576; n=9; filled red spotted boxes). A genotype difference was observed at t37.5 ($P2rx2^{(+/+)}$ vs. $P2rx2^{(-/-)}$, P=0.021). Boxplot in C of FIG. 11 includes data overlay (open circles). Dashed lines show the mean; solid lines show the median. Error bars represent the 95th percentile. See Table 2 for a more comprehensive statistical analysis.

TABLE 2

16 kHz ABR growth function and I/O gain for Study 1.

| | 16 kHz ABR growth function | | | | | 16 kHz ABR I/O gain | |
|---|---|---|---|---|---|---|---|
| | Treatment | | | | | | |
| | Noise | | | | | Noise | |
| | | | | | Genotype | | |
| Time point | $P2rx2^{(++)}$ | $P2rx2^{(-/-)}$ | $P2rx2^{(++)}$ | $P2rx2^{(-/-)}$ | $P2rx2^{(+/+)}$ vs. $P2rx2^{(-/-)}$ (at t37.5) | | $P2rx2^{(+/+)}$ vs. $P2rx2^{(-/-)}$ |
| t0 vs. t37.5 | 0.003 | 0.607 (n.s.) | 0.002 | 0.576 (n.s.) | 0.021 | Overall effect | 0.08 (n.s.) |

Our results show that in the $P2rx2^{(+/+)}$ mice, there was a progressive decrease in the N1-P2 amplitude and slope measured between 30 dB SPL and 50 dB SPL up to ~17.5 minutes, which reflects a decrease in gain during noise (t0=0.0451±0.0048 µV/dB; t37.5=0.0310±0.0035 µV/dB; P=0.002, two-way repeated measures ANOVA, n=11) (FIG. 11 plot C; Table 2). In contrast, in the $P2rx2^{(-/-)}$ mice, the gain was unchanged during the noise exposure period (t0=0.0450±0.0046 µV/dB; t37.5=0.0497±0.0053 µV/dB; P=0.576, two-way repeated measures ANOVA; n=9) (FIG. 11 plot C; Table 2). Overall, these results indicate that the cochlear nerve fibre recruitment is subject to purinergic hearing adaptation which is fully engaged by the 17.5 minutes cumulative noise exposure census point.

The $P2X_2R$-Mediated Hearing Adaptation Impacts on the 'Cochlear Amplifier'

Under k/x/a anaesthesia, Study 1 showed that $P2rx2^{(+/+)}$ mice have significant threshold shifts in cubic DPOAEs over the 37.5 minute cumulative 85 dB SPL noise regime compared to the $P2rx2^{(-/-)}$ mice (FIG. 12; Table 3; $P2rx2^{(+/+)}$ vs. $P2rx2^{(-/-)}$: P=0.004, genotype difference, two-way repeated measures ANOVA). FIG. 12 shows boxplots with data overlay (open circles) of the cubic (2f1-f2) DPOAE threshold shifts showing that P2rx2$^{(+/+)}$ mice (filled blue boxes) are significantly different to P2rx2$^{(-/-)}$ mice (filled red boxes) after 7.5, 17.5 and 37.5 minutes noise exposure (85 dB SPL 8-32 kHz). (t7.5, P=0.014; t17.5, P=0.003; t37.5, P=0.004). Dashed lines show the mean; solid lines show the median. Error bars represent the 95th percentile. See Table 3 for a more comprehensive statistical analysis.

circles) of the cubic (2f1-f2) DPOAE threshold shifts showing that P2rx2$^{(+/+)}$ mice (filled blue boxes) are significantly different to P2rx2$^{(-/-)}$ mice (filled red spotted boxes) after 7.5 and 17.5 minutes noise exposure (85 dB SPL 8-32 kHz). (t7.5, P=0.002; t17.5, P<0.001; P2rx2$^{(+/+)}$, n=8; P2rx2$^{(-/-)}$, n=6). There was no significant difference between the no-noise (silent) controls (diagonally striped boxes). Dashed

TABLE 3

16 kHz cubic (2f1-f2) DPOAE threshold shifts with k/x/a anaesthetic for Study 1.
Cubic (2f$_1$-f$_2$) DPOAE threshold shifts

| | Treatment | | | | | |
|---|---|---|---|---|---|---|
| | Noise | | | | Noise | |
| | | | Genotype | | | |
| Time point | P2rx2$^{(+/+)}$ vs. P2rx2$^{(-/-)}$ | P2rx2$^{(+/+)}$ (one sample t test) | P2rx2$^{(-/-)}$ (one sample t test) | Time point | P2rx2$^{(+/+)}$ | P2rx2$^{(-/-)}$ |
| t7.5 | 0.014 | 0.008 | 1.0 | t7.5 vs. t17.5 | 0.005 | 0.283 (n.s.) |
| t17.5 | 0.003 | =<0.001 | 0.563 (n.s.) | t7.5 vs. t37.5 | <0.001 | <0.001 |
| t37.5 | 0.004 | =<0.001 | 0.001 | t17.5 vs. t37.5 | <0.001 | <0.001 |

The P2X$_2$R-Mediated Hearing Adaptation Occurs at the Cochlear Amplifier, as Evident from DPOAE Threshold Shifts Study 2 investigated whether the DPOAE sensitivity, which reflects outer hair cell-based cochlear amplifier function, showed adaptation at the 7.5 minute and 17.5 minute noise exposure intervals. The DPOAE thresholds were resolved at higher resolution (2.5 dB f1/f2 increments) in Study 2 using isoflurane anaesthesia, as it has been shown that while ketamine-based anaesthetics are ideal for ABR measurements, the anaesthetic agent can affect DPOAEs, and isoflurane provides better DPOAE stability. FIG. 13 and Table 4 show the significant cubic (2f1-f2) DPOAE threshold shifts in response to noise in the P2rx2$^{(+/+)}$ cohort, which did not occur with the P2rx2$^{(-/-)}$ cohort (p=0.004, genotype with noise; n=8, P2rx2$^{(+/+)}$, n=6, P2rx2$^{(-/-)}$; two-way RM ANOVA). FIG. 13 shows boxplots with data overlay (open lines show the mean; solid lines show the median. Error bars represent the 95th percentile. See Table 4 for a more comprehensive statistical analysis. FIG. 13 and Table 4 show the significantly greater cubic (2f1-f2) DPOAE threshold shifts in response to noise in the P2rx2$^{(+/+)}$ cohort compared with the P2rx2$^{(-/-)}$ cohort (p=0.004, genotype with noise, two-way repeated measures ANOVA) using isoflurane.

TABLE 4

16k Hz cubic (2f1-f2) DPOAE threshold shifts with isoflurane anaesthetic for Study 2.
Cubic (2f$_1$-f$_2$) DPOAE threshold shifts

| | Treatment | | | | | | | | |
|---|---|---|---|---|---|---|---|---|---|
| | Silent vs. Noise | Silent vs. Noise | Silent | Noise | Noise | Noise | | Noise | |
| | | | | | Genotype | | | | |
| Time point | P2rx2$^{(++)}$ P2rx2$^{(++)}$ | P2rx2$^{(-/-)}$ | P2rx2$^{(++)}$ vs. P2rx2$^{(-/-)}$ | P2rx2$^{(++)}$ vs. P2rx2$^{(-/-)}$ | P2rx2$^{(+/+)}$ (one sample t test) | P2rx2$^{(-/-)}$ (one sample t test) | Time point | P2rx2$^{(++)}$ | P2rx2$^{(-/-)}$ |
| t7.5 | <0.001 | 0.485 (n.s.) | 0.955 (n.s.) | 0.002 | =<0.001 | 0.012 | t7.5 vs. t17.5 | 0.058 (n.s.) | 0.587 (n.s.) |
| t17.5 | <0.001 | 0.165 (n.s.) | 0.778 (n.s.) | <0.001 | 0.008 | 0.019 | — | — | — |

As for the ABR (Study 1), the DPOAE threshold shift was significant at 7.5 minutes after noise exposure (t7.5; 6.04 dB greater threshold shift in P2rx2$^{(+/+)}$ relative to P2rx2$^{(-/-)}$, p=0.002; two-way RM ANOVA). The silent (unexposed) controls for the groups exhibited no change across the test period for either genotype (p=0.833; two-way RM ANOVA; FIG. 3). Furthermore, the noise-exposed ears of the P2rx2$^{(-/-)}$ mice showed no significant difference in DPOAE thresholds when compared to the opposite no-noise treated silent control) ears (t7.5, p=0.485; t17.5, p=0.165; n=6; two-way RM ANOVA). In contradistinction, the P2rx2$^{(+/+)}$ noise-treated ears were significantly different from the opposite unexposed (silent) control ears (t7.5, p<0.001; t17.5, p<0.001; n=8; two-way RM ANOVA) (Table 2).

Analysing the cubic (2f1–f2) DPOAE growth function provided a direct readout of the gain of the cochlear amplifier. FIG. 14a shows examples of the cubic (2f1–f2) DPOAE amplitude measured with an f1 and f2 input levels of 40 dB SPL, at baseline and after 7.5 and 17.5 minutes of cumulative noise exposure for both genotypes. Table 5 provides the statistical analysis, which confirmed the significant difference of the DPOAE amplitudes at this input level between genotypes after 7.5 and 17.5 minutes of noise exposure (P2rx2$^{(+/+)}$ vs. P2rx2$^{(-/-)}$: t7.5, p=0.004; t17.5, p=0.05; n=8 and 6, respectively; two-way RM ANOVA on Ranks).

p=0.016; P2rx2$^{(+/+)}$ t17.5 vs. P2rx2$^{(-/-)}$ t17.5, p=0.004; n=8; two-way ANOVA on Ranks). These data show a direct correlation between P2X$_2$R-mediated adaptation of hearing sensitivity measured by ABR threshold shift and cubic DPOAE threshold shift, both of which are largely complete within 7.5 minutes of noise exposure, and that this adaptation is evident as a right-shift in the input-output function of the P2rx2$^{(+/+)}$ DPOAE. These data indicate that the adaptation is primarily derived from a reduction in sensitivity of electromechanical transduction at the outer hair cell-based cochlear amplifier, rather than at the primary auditory synapses at the level of the inner hair cells.

TABLE 5

16k Hz cubic (2f1-f2) DPOAE amplitudes and growth function for Study 2.
16 kHz cubic (2f$_1$-f$_2$) DPOAE amplitudes with an f$_1$ and f$_2$ input level of 40 dB SPL*

| | Treatment | | | | |
| --- | --- | --- | --- | --- | --- |
| | Noise | | | Noise Genotype | |
| Time point | P2rx2$^{(+/+)}$ | P2rx2$^{(-/-)}$ | Time point | P2rx2$^{(+/+)}$ vs. P2rx2$^{(-/-)}$ | P2rx2$^{(+/+)}$ (FIG. 4a example; dB) | P2rx2$^{(-/-)}$ (FIG. 4a example; dB) |
| t0 vs. t7.5 | <0.001 | 0.341 n.s | t0 | 0.907 n.s | 29.61 | 24.83 |
| t0 vs. t17.5 | <0.001 | 0.044 | t7.5 | 0.004 | 18.83 | 23.48 |
| t7.5 vs. t17.5 | 0.537 n.s | 0.208 n.s | t17.5 | 0.05 | 19.92 | 21.45 |

| 16 kHZ cubic (2f$_1$-f$_2$) DPOAE growth function$^\#$ | | | | | |
| --- | --- | --- | --- | --- | --- |
| | Noise | | | | Noise Genotype |
| Time Point | P2rx2$^{(+/+)}$ | P2rx2$^{(-/-)}$ | P2rx2$^{(+/+)}$ vs. P2rx2$^{(-/-)}$ | Time point | P2rx2$^{(+/+)}$ vs. P2rx2$^{(-/-)}$ |
| t0 vs. t7.5 | <0.001 | 0.927 n.s | — | t0 | 0.909 n.s |
| t0 vs. t17.5 | <0.001 | 0.024 | — | t7.5 | <0.001 |
| t7.5 vs. t17.5 | 0.859 n.s | 0.121 n.s | 0.016 | T17.5 | 0.004 |

There was no difference in the DPOAE amplitudes before noise exposure between genotypes (t0, p=0.907). Overall change in growth function across the time census points between the P2rx2$^{(+/+)}$ and P2rx2$^{(-/-)}$ cohorts was also analysed and showed a significant difference (p<0.001; n=8 for each genotype; f1 & f2 input levels of 35-55 dB SPL; Two-way ANOVA on Ranks; FIGS. 14b and c, Table 5). While the growth function for the P2rx2$^{(+/+)}$ mice is maximally shifted to the right after 7.5 minutes of noise (t0 vs. t7.5, p<0.001; t7.5 vs. t17.5, p=0.859; n=8; Two-way ANOVA on Ranks; FIG. 14b), this did not hold for the P2rx2$^{(-/-)}$ mice (t0 vs. t7.5, p=0.927; t7.5 vs. t17.5, p=0.121; n=8; Two-way ANOVA on Ranks; FIG. 14c). Furthermore, although the growth function of the P2rx2$^{(-/-)}$ mice was significantly different after 17.5 minutes of noise to that prior to noise exposure (t0 vs. t17.5, p=0.024; n=8; two-way ANOVA on Ranks; dB SPL -55 dB SPL input level), the level of rightward shift is significantly smaller than that of the P2rx2$^{(+/+)}$ mice (P2rx2$^{(+/+)}$ t7.5 vs. P2rx2$^{(-/-)}$ t17.5, Fine Temporal Resolution of P2X$_2$R-Mediated Hearing Adaptation from ABR Studies 1 & 2 confirmed that the P2X$_2$R-mediated hearing adaptation was largely complete by 7.5 minutes of noise exposure. In Study 3, the inventors undertook a finer temporal examination of the onset of the adaptation. The mean ABR thresholds for the P2rx2$^{(+/+)}$ mice under k/x/a anaesthesia increased from 3.8±1.4 dB SPL, to 9.6±2.0 dB SPL after 5 minutes noise (p=0.001, two-way RM ANOVA, n=6). After 10 minutes noise, the mean ABR threshold was 14.6±1.9 dB SPL (t5 vs. t10, p=0.015). FIG. 15 shows ABR threshold shifts (subtracting the baseline threshold from either the t5 or t10 thresholds for each mouse), with ~50% of the TTS occurring by t5. The P2rx2$^{(-/-)}$ mice (n=6) had equivalent baseline thresholds (5.4±3.1 dB SPL; p=0.903 vs. t0 for P2rx2$^{(+/+)}$ mice; two-way RM ANOVA). The P2rx2$^{(-/-)}$ mouse thresholds were 7.1±2.6 dB SPL at t5; 9.2±2.7 at t10, with no significant change in threshold shifts between t5 and t10 (p=0.055; FIG. 15).

TABLE 6

16 kHz ABR thresholds and threshold shifts for Study 3.

16 kHz ABR thresholds

| | Treatment | | | | | |
|---|---|---|---|---|---|---|
| | Noise | | | Noise | | |
| | | | | Genotype | | |
| Time point | $P2rx2^{(+/+)}$ | $P2rx2^{(-/-)}$ | Time point | $P2rx2^{(+/+)}$ vs. $P2rx2^{(-/-)}$ | $P2rx2^{(+/+)}$ (dB SPL) | $P2rx2^{(-/-)}$ (dB SPL) |
| t0 vs. t5 | 0.002 | 0.450 (n.s.) | t0 | 0.611 (n.s.) | 4.4 ± 1.9 | 6.9 ± 4.5 |
| t5 vs. t10 | 0.004 | 0.268 (n.s.) | t5 | 0.527 (n.s.) | 11.2 ± 2.6 | 8.1 ± 4.0 |
| t0 vs. t10 | <0.001 | 0.107 (n.s.) | t10 | 0.224 (n.s.) | 16.9 ± 1.9 | 10.6 ± 4.0 |

16 kHz ABR threshold shifts

| | Treatment | | | | |
|---|---|---|---|---|---|
| | Noise | | | | |
| | Genotype | | | | |
| Time point | $P2rx2^{(+/+)}$ vs. $P2rx2^{(-/-)}$ | $P2rx2^{(+/+)}$ (one-sample t test) | $P2rx2^{(-/-)}$ (one-sample t test) | $P2rx2^{(+/+)}$ (dB) | $P2rx2^{(-/-)}$ (dB) |
| t5 | 0.05 | *0.038 | #0.5 (n.s.) | 6.9 ± 2.6 | 1.3 ± 0.7 |
| t10 | 0.007 | **0.003 | **0.125 (n.s.) | 12.5 ± 1.8 | 3.8 ± 1.3 |

TABLE 7

16k Hz cubic (2f1-f2) DPOAE amplitudes and reduction for Study 3.

| | 16 kHz cubic $(2f_1-f_2)$ DPOAE amplitudes with $f_1$ and $f_2$ input level of 60 dB SPL | | | | | | | 16 kHz cubic $(2f_1-f_2)$ DPOAE reduction |
|---|---|---|---|---|---|---|---|---|
| | Treatment | | | | | | | |
| | Noise | | | | Noise | | | Noise |
| | Genotype | | | | | | | |
| Time point | $P2rx2^{(+/+)}$ vs. $P2rx2^{(-/-)}$ | $P2rx2^{(+/+)}$ (dB) | $P2rx2^{(-/-)}$ (dB) | Time point | $P2rx2^{(+/+)}$ | $P2rx2^{(-/-)}$ | Time point | $P2rx2^{(+/+)}$ vs. $P2rx2^{(-/-)}$ |
| t0 | 0.029 | 22.6 ± 1.7 | 26.6 ± 0.7 | — | — | — | — | — |
| t2.5 | <0.001 | 16.8 ± 1.5 | 24.6 ± 0.9 | t0 vs. t2.5 | <0.001 | 0.094 (n.s.) | t2.5 | 0.023 |
| t5 | <0.001 | 14.5 ± 1.4 | 22.3 ± 0.7 | t0 vs. t5 | <0.001 | 0.001 | t5 | 0.024 |
| t7.5 | <0.001 | 13.1 ± 1.1 | 21.9 ± 0.2 | t0 vs. t7.5 | <0.001 | <0.001 | t7.5 | 0.007 |

Fine Temporal Resolution of P2X$_2$R-Mediated Hearing Adaptation from DPOAE

As the cubic (2f1-f2) DPOAE recordings required less signal averaging than the ABR recordings, it was practical to measure the P2X$_2$R-mediated hearing adaptation at 2.5 minute noise exposure separations. This analysis used the same mice as for the Study 3 ABR experiments, experiments, with isoflurane anaesthesia (n=6 per group). The DPOAEs were elicited using 60 dB SPL f1 and f2 drivers. As shown in FIG. 15 pane C, the P2rx2$^{(+/+)}$ mice and P2rx2$^{(-/-)}$ mice had comparable initial amplitudes (t0) of 25.9±2.3 dB and 28.2±1.9 dB respectively (p=0.66; unpaired t-test). The P2rx2$^{(+/+)}$ and P2rx2$^{(-/-)}$ mouse DPOAEs diverged with noise (20.6±2.6 dB vs. 26.3±2.2 dB (t2.5); 18.3±2.6 dB vs. 24.2±2.1 dB (t5); 17.3±2.8 dB vs. 23.5±2.0 dB (t7.5). The overall genotype effect (P2rx2$^{(+/+)}$ vs. P2rx2$^{(-/-)}$) across the three noise exposure census points for this study was significant (p=0.013; two-way RM ANOVA; FIG. 15D), with the difference in reduction significant from the initial 2.5 minute time point (5.3±0.9 dB vs. 1.9±0.6 dB for t2.5, P2rx2$^{(+/+)}$ vs. P2rx2$^{(-/-)}$; p=0.019, two-way RM ANOVA). The noise-induced adaptation of the DPOAE output in the P2rx2$^{(+/+)}$ mice was best fitted by a single exponential decay function $f=-9.30+9.30e^{-0.326x}$ ($R^2=1.0$) (FIG. 15D), where the derived time constant ($\tau$)=2.96 minutes, reconciles well with the rate of adaptation evident in Studies 1 to 3. In contrast, the P2rx2$^{(-/-)}$ mice exhibited a significantly smaller linear drift in DPOAE over time ($f=-0.237-0.654x$; $R^2=0.96$).

FIG. 16 shows modelling of kinetics of purinergic adaptation from ABR threshold shifts during noise exposure.

Best fit single exponential fit to the growth of the ABR threshold shift with cumulative broadband noise exposure (85 dB SPL; combined ABR data from all three studies; mean±S.E.M.; n=6-12). P2rx2$^{(+/+)}$ mice 1610 (wildtype, WT; blue squares), f=9.66(1-e-0.180x) (black solid line; $R^2$=0.45), corresponding to a time constant ($\tau$)=5.5 minutes; P2rx2$^{(-/-)}$ mice 1620 (knockout, KO; red circles), f=4.72 (1−e−0.088x) (black dashed line; $R^2$=0.74), corresponding to $\tau$=11.3 minutes (P2rx2$^{(+/+)}$ vs. P2rx2$^{(-/-)}$, p<0.001; two-way ANOVA on Ranks on differences between means across time points). Inset, P2rx2-specific development of the ABR (P2rx2$^{(-/-)}$ data subtracted from P2rx2$^{(+/+)}$ data; f=5.31 (1−e$^{-0.289x}$)), corresponding to $\tau$=3.46 minutes. Green bars 1630 indicate noise exposure.

FIG. 17 illustrates development of the cubic (2f1−f2) DPOAE adaptation with noise exposure in a human subject. Pane A shows comparison of the reduction in the DPOAE output probing the 4 kHz region of the cochlea using two different noise levels (92 dBA (triangle, right ear) and 98 dBA (diamond, left ear) using L1=60 dB SPL. The hearing adaptation was largely complete within 7.5 minutes of cumulative noise, which is comparable to the P2X$_2$R-dependent adaptation in the mouse studies. Black stars are the average of left and right ears tested 18 days after the noise test, as a no-noise control to show stability of the DPOAE recordings and to validate recovery of hearing sensitivity. FIG. 17 pane B shows data for the same two noise exposure levels indicated in pane A, but using a stronger driver (L1=65 dB SPL) (square, right ear; circle, left ear; star—average of left and right ears for subsequent no-noise control measurements). FIG. 17 pane C shows the adaptation of hearing sensitivity during 17.5 minutes of cumulative noise exposure in the human, calculated using data from pane A and pane B, determined from the cubic DPOAE data by subtracting the DPOAE amplitude at each time point from the corresponding baseline (t0) value (open symbols). This was best fitted by a single exponential decay function (solid line; filled circles with error bars show mean±S.E.M.) f=−7.80+7.95e−0.156x ($R^2$=0.99), with time constant ($\tau$)=6.42 minutes; which is comparable to the kinetics for reduction in DPOAE amplitude in the P2rx2$^{(+/+)}$ mice with noise exposure (FIG. 15D). L2=L1−10 dB SPL.

These three mouse studies resolved the onset kinetics of P2X$_2$R-dependent hearing adaptation to noise exposure, finding that the time constant was ~3 minutes, whether measured by ABR threshold shift, or reduction in cubic DPOAE amplitude. This is much faster than previous analysis of P2X$_2$R-dependent adaptation of ABR thresholds ($\tau$~20 minutes) which was based on ABR threshold measurements commencing after 10 minutes of noise and extending to two hours of cumulative noise exposure. The inventors have shown that the noise-induced increase in the ABR thresholds in the wildtype mice is largely complete by 7.5 minutes, whereas minor non-P2rx2-dependent drift in thresholds (evident in the P2rx2$^{(-/-)}$ mice) had slower kinetics, that evidently confounded the original estimate. The finding that the adaptation rate of the cubic DPOAE matches the adaptation of the ABR indicates that this reversible noise-induced loss of hearing sensitivity lies with the cochlear amplifier. Evidently, noise-induced release of ATP from the cochlear partition tissues activates organ of Corti P2X$_2$R-type ATP-gated ion channels, which in turn produces a temporary reduction in the cochlear amplifier gain. While P2X$_2$R are also expressed by the spiral ganglion neurons, the data do not support a potential neuromodulatory action on auditory neurotransmission as a contributor to the noise-induced ABR threshold shift.

While the inventors' studies make it clear that changes in the cochlear amplifier are responsible for purinergic hearing adaptation to noise, the actual mechanism has yet to be determined. Injection of ATP into the cochlear scala media chamber in guinea pigs and mice elicits an increase in conductance across the cochlear partition, and this is absent in the P2rx2$^{(-/-)}$ mice; indicating that P2X$_2$Rs are the only ATP-gated ion channels and the exclusive transepithelial current shunt pathway for purinergic signalling in the cochlea. The outer hair cells must be a major component of this ATP signalling pathway, as they have been found to have high expression levels of ATP-gated ion channels functionally localised to the endolymph-facing apical (sensory) pole, and in the P2rx2$^{(-/-)}$ mice, voltage-clamp studies found a complete loss of ATP-activated current, indicating that in the wildtype outer hair cells, the ion channels are only assembled from P2X$_2$R subunits. The electromotile properties of the outer hair cells underlie dynamic cochlear micromechanics, referred to as the cochlear amplifier, which confers the up to ~40 dB of hearing sensitivity. It has been suggested that the ATP-gated shunt conductance across the outer hair cells may be a paracrine signalling mechanism controlling cochlear amplifier gain. However, activation of the P2X$_2$R in the cochlear partition by noise-induced ATP release would be limited to the duration of the noise exposure, due to the rapid hydrolysis of released ATP by extracellular nucleotidases. This is evident from the recovery of the endocochlear potential (EP) within minutes following injection of ATP into the scala media. In contrast, the recovery of the noise-induced P2X2R-mediated ABR TTS has a time constant of 12.3 hours, which indicates that the sustained suppression of the cochlear amplifier gain involves long-acting secondary mechanisms activated by ATP-gated ion channels. Given that the supporting cells surrounding the outer hair cells also express P2X2R, noise-induced activation of the ATP-gated ion channels in those cells (particularly Deiters' cells) may well contribute to the sustained suppression of the cochlear micromechanics, possibly mediated by Ca2+ signalling.

It is also possible the EP contributes to the purinergic hearing adaptation, however, the EP is not subject to sustained changes following noise at the levels used here that selectively activate the P2X2R-specific threshold shifts. The EP is a biopotential within scala media (~+100 mV) that complements the negative membrane potential of the hair cells to provide the driving force for outer hair cell forward and reverse transduction. Many studies, using guinea-pigs or mice, have shown that the much higher noise levels than those used in the present study are required to cause a sustained drop in EP (~98 dB SPL). Moreover, studies have shown that despite a temporary threshold shift of 40 dB after 94 dB SPL noise exposure for 2 hours, the EP was unaffected in CBA/CaJ mice. Similar results have been observed where it has been reported that the EP in C57Bl/6 mice (the strain used in the current study) was unaffected by noise until 110 dB SPL (supported by earlier studies).

Purinergic hearing adaptation, which is a sustained local cochlear paracrine humoral mechanism, complements the more sensitive and dynamic medial olivocochlear efferent system which causes contralateral and ipsilateral suppression of the cochlear amplifier as a negative feedback neural circuit driven by input from the type II spiral ganglion innervation of the outer hair cells [9]. The suppression of the outer hair cells by the medial olivocochlear efferents engages in the sub-second time domain at moderate to loud sound levels (tending to saturate around 85 dB SPL), exhibits adaptation within seconds, is mapped to the exposure sound frequency to modulate auditory nerve firing and confers protection from noise-induced hearing loss. In the current study, ipsilateral medial olivocochlear efferent suppression (due to close-field noise presentation to the test ear) may have contributed to the background adaptation of the cubic DPOAE measurements (FIG. 15C-D, P2rx2$^{(-/-)}$ mice), but this would have been less than 3 dB, based on a study using quadratic (f2−f1) DPOAE measurements, which are more sensitive at measuring olivocochlear efferent suppression.

Evidently, purinergic adaptation to noise engages broadly towards the upper physiological levels of sustained sound exposure, where basilar membrane mechanics are dominated by the physical properties of its component structures. At these levels, purinergic suppression of the cochlear amplifier effectively extends the dynamic range for encoding sound. The physical stress of sound vibration is likely to be the driver for release of ATP from the tissues lining the cochlear partition, via vesicles and through connexins and pannexin channels. With prolonged noise exposure above physiologic levels, purinergic adaptation can protect the organ of Corti from intrinsic overstimulation which leads to glutamate excitotoxicity at the spiral ganglion neurons and wider sensorineural pathophysiology. This is evident from acute and chronic studies of the hearing in P2rx2$^{(-/-)}$ mice exposed to loud noise. P2rx2$^{(-/-)}$ mice developed permanent hearing loss after only 30 minutes of 95 dB SPL 8-16 kHz band noise, while the same exposure has no permanent impact on wildtype controls. Similarly, chronic exposure to environmental level noise (75 dB SPL) up to 17 months of age produced accelerated high-frequency hearing loss, as well as organ of Corti hair cell and supporting cell loss, in P2rx2$^{(-/-)}$ mice, but not in wild-types.

The vulnerability of the cochlea to acoustic overstimulation in the absence of P2X$_2$R expression can be extended to the human condition. Alongside the evaluation of purinergic adaptation to noise in the P2rx2$^{(-/-)}$ mouse model, loss of function of the P2X2R was identified in two independent Chinese families previously characterized as having DNFA41 autosomal dominant progressive sensorineural hearing loss, where a c.178G>T (p.V60L) point mutation in the P2RX2 gene co-segregated with the DFNA41-based hearing loss. Loss of function was determined by the absence of ATP-gated inward cation current in recombinant HEK293 cells expressing this mutation. The mutation carriers exhibited progressively worsening hearing loss over forty years, ending with profound hearing loss (>50 dB HL), with a record of exposure to environmental noise exposure exacerbating this hearing loss at higher frequencies (>1 kHz), reminiscent of the findings in homozygous P2rx2$^{(-/-)}$ mice in noisy as compared to quiet environmental chambers. While mutations in the P2RX2 gene appear to be rare, additional mutations have subsequently been identified through deep sequencing after diagnosis of hearing loss. This includes a missense mutation (p.Gly353Arg) in an Italian family, and a c.601G>A (p.Asp201Tyr) mutation detected in two members of a family in the Nagano region of Japan.

Within human populations, genetic variance across all the associated aspects of the P2X$_2$R signalling cascade, including ATP release mechanisms (such as variance in pannexin hemichannels), extracellular ATP hydrolysis (variance in ecto-ATPases), alongside the emerging variance in P2X2R-type ATP-gated ion channel properties, are likely to contribute to the broad differential vulnerability to noise-induced hearing loss. The expansion of knowledge on functional genomics of these signalling elements in human populations will facilitate further development of transgenic mouse models for probing the physiology around purinergic hearing adaptation.

The inventors' test data strongly support the idea that purinergic hearing adaptation to sustained elevation in sound levels occurs upstream of the inner hair cell—spiral ganglion synapses, and that the most likely mechanism involves the reduction in sensitivity of outer hair cell-based cochlear amplifier. They also demonstrate that this adaptation process is fully engaged within a few minutes of noise exposure.

The present study validated baseline stability of ABR and DPOAE hearing sensitivity by mock noise exposure and by optimising the k/x/a and isoflurane anaesthesia to the respective hearing test modalities. The (complete) recovery from this P2X$_2$R-specific noise adaptation was characterised in our earlier study and found to have a time constant of 12 hours. This was validated in the present study by retesting the mice in the days following noise exposure with ABR and DPOAE testing to confirm recovery of thresholds.

Purinergic hearing adaptation is clearly integral to the phenomenon of TTS, reflecting reversible hearing loss from exposure to moderate to high noise levels. In animal models, TTS has been studied across a range of sound intensity/duration and frequency bands and the implicated physiological processes reflect broad integration of cochlear physiology. For example, presentation of high intensity noise bursts of less than 100 ms duration in guinea pigs caused reversible reductions in basilar membrane vibration that were found to stem directly from altered outer hair cell micromechanics, rather than reduction in hair cell transducer currents. This was independent of middle ear reflexes or olivocochlear efferent suppression which provide dynamic reduction of hearing sensitivity both ipsilaterally and contralaterally when loud sound is presented to the ear. The middle ear reflex is considered to be primarily otoprotective with vocalization. The efferents support rapid and dynamic filtering of sound transduction which contributes to masking background sound, which in humans, enables speech perception against background noise. Other studies have titrated noise exposure (intensity/time) to assess levels of ABR threshold shift and time for recovery and linked this to analysis of the contribution of the medial olivocochlear efferent innervation of the outer hair cells, to determine the contribution of this CNS reflex pathway to protection from permanent noise-induced hearing loss. Transgenic mice overexpressing the outer hair cell α9 cholinergic efferent receptor that mediates efferent suppression showed that acoustic injury was significantly reduced. There is evidently a fine line between TTS and PTS as TTS level noise exposure in juvenile mice leads to PTS at a later age.

The role of purinergic hearing adaptation, which is a local cochlear paracrine humoral mechanism, complements the more sensitive olivocochlear efferent system. The rapidly adapting efferent suppression of the cochlear amplifier outer hair cells engages in the sub-second time domain at low to moderate sound levels and saturates around the point of maximum input of the cochlear amplifier to regulate sensitivity of frequency selectivity of vibration of the basilar membrane (40-60 dB SPL). Based on the current finding that the cochlear amplifier underlies purinergic adaptation to noise, this system evidently picks up the role of suppression of the outer hair cell electromotility in a broader modality at moderate to high physiological sound levels, at which the cochlear basilar membrane mechanics are dominated by the physical properties of structures and at which broad suppression of the cochlear amplifier effectively extends the dynamic range for encoding sound. Purinergic signalling also protects the organ of Corti from intrinsic overstimulation which leads to glutamate excitotoxicity at the spiral ganglion neurons and wider sensorineural pathophysiology, evident from acute and chronic studies of the hearing in P2rx2$^{(-/-)}$ mice exposed to moderate/loud noise. These P2rx2$^{(-/-)}$ mice developed profound permanent hearing loss after only two hours of 100 db SPL 16 kHz octave band noise, with little impact on the wild-type controls, while chronic exposure to environmental level noise (75 dB SPL) up to 17 months of age produced enhanced auditory neuropathy evident as high frequency hearing loss, and accelerated organ of Corti hair cell and supporting cell loss.

This study has determined that the purinergic hearing adaptation mechanism is based on noise-induced ATP release acting on P2X$_2$R that affect cochlear outer hair cell transduction; that is, upstream of the inner hair cells and the type I spiral ganglion afferents, all of which express these receptors. A key finding of our earlier study of the P2rx2$^{(-/-)}$ mouse model was the lack of compensation for the knockout of the gene. Neither outer hair cells, inner hair cells or Reissner's membrane epithelial cells in these mice exhibited ATP-gated membrane currents, suggesting that in the wild-type mice, the ATP-gated ion channels are trimeric homomers of the P2X$_2$R subunit alone. This is also consistent with cochlear partition resistance measurements in these mice, where injection of ATP solution into scala media (endolymph), which is matched to the polar targeting of these ion channels in the sensori-epithelium, produced substantial reductions in the cochlear partition resistance in the wild-type mice but no change in the P2rx2$^{(-/-)}$ mice. Hence, the P2X$_2$R is the dominant cochlear purinergic conductance in this species. Across guinea pig and mouse outer hair cells, the ATP-gated ion channels have been functionally localized to the apical pole, matching P2X$_2$R immunolabelling. In guinea pig outer hair cells, this ATP-gated conductance is tonotopically regulated to parallel the increasing basolateral K+ conductance which develops towards the high frequency encoding basal region, and would therefore provide equivalent conductive offset to the K+ conductance across the full span of the organ of Corti. On that basis, noise-induced release of ATP into the endolymph, which may be vesicular, or via paracellular pathways involving connexin and pannexin hemichannels, may invoke activation of the cochlear partition P2X2R conductance that shunts the K+-dominated cation flux across the cochlear partition, of which the outer hair cell ATP-gated conductance is a significant component. However, this extracellular ATP conductance would cease as sound levels return to ambient, ATP release ceases and free extracellular ATP is hydrolysed by ectonucleotidases.

The evident paradox is therefore that while the P2XR is the upstream element of this purinergic hearing adaptation mechanism, and mediates a noise-induced reduction in basilar membrane compliance that is dependent upon reduced outer hair cell electromotility, these receptors would be deactivated soon after the noise ceases, but the recovery of the hearing adaptation is sustained for many additional hours.

With regard to the purinergic adaptation of the cochlear amplifier evident in the reduction DPOAE signal over time with noise exposure, or the elevation of the DPOAE threshold, or indeed the change in threshold or reduction in the input-output function of ABR measurements during noise exposure, the adaptation parameters are evidently directly linked to activation of P2X$_2$ receptors expressed by cells in the cochlea, impacting on the cochlear amplifier, but the variance in this signalling mechanism, and hence the intrinsic vulnerability of an individual to hearing loss from noise exposure, may also arise from changes in other aspects of the process that leads to activation of the P2X$_2$ receptor ATP-gated ion channels. This may include, but not be limited to: alterations in the capacity of the cochlear cells to release ATP in response to the onset of elevation in sound levels, mechanisms that control the trafficking of P2X$_2$R to the cell membrane, or rate of breakdown of the extracellular ATP by the ectonucleotidase enzymes on the cell membranes or within the cochlear fluids. It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:

1. An audiometric test method comprising:
    applying a noise stimulus to a subject for a duration of at least two minutes to drive purinergic hearing adaption and applying a second stimulus in the form of two pure tones;
    during the application of the noise stimulus and/or second stimulus, measuring one or more indicators reflecting a subject's purinergic hearing adaptation to noise exposure; and
    analysing the measured indicators to quantify degree of change and rate of change of the subject's purinergic hearing adaptation to noise exposure from the noise stimulus.

2. An audiometric test method as claimed in claim 1, wherein one of the one or more measured indicators is otoacoustic emissions, and the measured otoacoustic emissions are analysed to quantify change in amplitude and rate of change of the otoacoustic emissions during noise stimulus.

3. An audiometric test method as claimed in claim 2, further comprising:
    quantifying the subject's reduction in noise sensitivity over the course of the noise stimulus based on the subject's otoacoustic emissions; and
    outputting a measure indicative of the subject's vulnerability to noise-induced hearing loss.

4. An audiometric test method as claimed in claim 2, wherein:
    the application of the second stimulus comprises one or more iterations of concurrently presenting the two pure tones, wherein the two pure tones are separated by a defined ratio (f1:f2) for a predetermined time period; and
    performing the measuring using a microphone to collect sound from the outer ear canal to measure a third tone (f3), which is a resultant distortion product otoacoustic emission (DPOAE) stimulated by the presented tones (f1, f2).

5. An audiometric test method as claimed in claim 4, wherein the ratio of the two DPOAE probe tones is 1.2 (f1=1.2f2).

6. An audiometric test method as claimed in claim 4, wherein the noise stimulus and/or second stimulus comprises two or more iterations with the intensity of the presented tones incremented between iterations.

7. An audiometric test method as claimed in claim 1, wherein the noise stimulus comprising any one of: white noise, Gaussian noise, pure tones, clicks, or any combination thereof, or a combination of sampled sounds of natural or synthetic source.

8. An audiometric test method as claimed in claim 1, test further comprising:
an initial step of identifying a threshold intensity for the subject to elicit measurable distortion product otoacoustic emission (DPOAE) response; and
setting initial intensity levels for the noise stimulus and/or second stimulus test based on this threshold.

9. An audiometric test method as claimed in claim 8, further comprising:
determining the threshold intensity by applying a sound signal having increasing intensity; and
using a microphone to record elicited DPOAE response.

10. An audiometric test method as claimed in claim 8, further comprising:
determining the threshold intensity by applying a sound signal having increasing intensity; and
using a camera or other non-auditory pickup, wherein the other non-auditory pickup includes a laser doppler or ultrasonics, to monitor for an elicited response within the outer, middle or inner ear.

11. An audiometric test method as claimed in claim 1, further comprising applying a noise adaptation index to determine a measure indicative of the subject's vulnerability to noise-induced hearing loss based on the subject's reduction in noise sensitivity over the course of the application of the noise stimulus and/or second stimulus.

12. An audiometric test method as claimed in claim 1, wherein:
one of the one or more measured indicators is a subject's auditory brainstem response (ABR),
the measured ABR is analysed to quantify extent and rate of change during noise exposure; and
the ABR is measured using either penetrating or surface electrodes.

13. An audiometric test system comprising:
a sound generator configured to deliver a noise stimulus to drive purinergic hearing adaptation, for a duration of at least two minutes to a subject and a second stimulus in the form of two pure tones to enable measurement of distortion product otoacoustic emissions (DPOAE);
one or more sensor modules configured to record data measuring one or more indicators comprising changes in otoacoustic emissions reflecting a subject's purinergic hearing adaptation to noise exposure from the noise stimulus; and
a processor configured to drive the sound generator to deliver the noise stimulus and second stimulus, receive the recorded data and analyse the recorded data to quantify for one or more of the measured indicators degree of change and rate of change, and output data quantifying the subject's purinergic hearing adaptation to noise exposure from the noise stimulus,
wherein the measured otoacoustic emissions are analysed to quantify change in amplitude and rate of change of the otoacoustic emissions during the noise stimulus.

14. The audiometric test system as claimed in claim 13, wherein at least one of the one or more sensor modules are provided on a probe configured for insertion into the external ear canal of the subject.

15. The audiometric test system as claimed in claim 14, wherein the processor is further configured to quantify the subject's reduction in noise sensitivity over the course of the application of the noise stimulus and/or second stimulus based on the subject's otoacoustic emissions and outputting a measure indicative of the subject's purinergic hearing adaptation to noise exposure.

16. The audiometric test system as claimed in claim 15, further including a microphone, wherein the data measuring one or more indicators reflecting a subject's purinergic hearing adaptation to noise exposure comprises data from one or more iterations of concurrently presenting the second stimulus as two pure tones separated by a defined ratio (f1:f2) for a predetermined time period, and wherein the data measuring the one or more indicators reflecting a subject's purinergic hearing adaptation is collected using the microphone to collect sound from the outer ear canal to measure a DPOAE signal which is a resultant DPOAE stimulated by the presented tones (f1, f2).

17. The audiometric test system as claimed in claim 16, wherein the data measuring one or more indicators reflecting a subject's purinergic hearing adaptation to noise exposure comprises data from two or more iterations with the intensity of the presented tones incremented periodically.

18. The audiometric test system as claimed in claim 17, wherein the noise stimulus comprising any one of: white noise, Gaussian noise, pink noise, clicks, or any combination thereof, or a combination of sampled sounds of natural or synthetic source.

19. The audiometric test system as claimed in claim 17, wherein the data measuring one or more indicators reflecting a subject's purinergic hearing adaptation to noise exposure further comprises data of identifying a threshold intensity for the subject to elicit measurable DPOAE response, and setting initial intensity levels for the noise stimulus and/or second stimulus based on this threshold.

20. The audiometric test system as claimed in claim 13, wherein one of the one or more measured indicators is a subject's auditory brainstem response (ABR), and the measured ABR is analysed to quantify extent and rate of change during noise exposure, and wherein the ABR is measured using either penetrating or surface electrodes.

* * * * *